(12) United States Patent
Gardner

(10) Patent No.: US 7,286,970 B2
(45) Date of Patent: Oct. 23, 2007

(54) COMPUTATIONAL MODEL, METHOD, AND SYSTEM FOR KINETICALLY-TAILORING MULTI-DRUG CHEMOTHERAPY FOR INDIVIDUALS

(75) Inventor: Shea Nicole Gardner, San Leandro, CA (US)

(73) Assignee: The Regents of the University of California, Oakland, CA (US)

(*) Notice: Subject to any disclaimer, the term of this patent is extended or adjusted under 35 U.S.C. 154(b) by 272 days.

(21) Appl. No.: 10/338,559

(22) Filed: Jan. 7, 2003

(65) Prior Publication Data
US 2003/0144798 A1    Jul. 31, 2003

Related U.S. Application Data

(60) Provisional application No. 60/346,631, filed on Jan. 7, 2002.

(51) Int. Cl.
*G06N 3/10* (2006.01)
*G06G 7/60* (2006.01)
(52) U.S. Cl. ............................................. 703/2; 702/19
(58) Field of Classification Search ...................... None
See application file for complete search history.

(56) References Cited

U.S. PATENT DOCUMENTS

| | | | |
|---|---|---|---|
| 5,366,885 A | 11/1994 | Barranco, III | |
| 6,025,128 A | 2/2000 | Veltri et al. | |
| 6,317,731 B1 | 11/2001 | Luciano et al. | |
| 6,871,171 B1 * | 3/2005 | Agur et al. | ................... 703/11 |
| 2002/0065234 A1 | 5/2002 | Horwitz et al. | |
| 2002/0095258 A1 | 7/2002 | Agur et al. | |

OTHER PUBLICATIONS

Iliadis et al. (Computers and Biomedical Research (2000) vol. 33, pp. 211-226).*

* cited by examiner

*Primary Examiner*—Marjorie A. Moran
(74) *Attorney, Agent, or Firm*—James S. Tak; John H. Lee

(57) ABSTRACT

A method and system for tailoring treatment regimens to individual patients with diseased cells exhibiting evolution of resistance to such treatments. A mathematical model is provided which models rates of population change of proliferating and quiescent diseased cells using cell kinetics and evolution of resistance of the diseased cells, and pharmacokinetic and pharmacodynamic models. Cell kinetic parameters are obtained from an individual patient and applied to the mathematical model to solve for a plurality of treatment regimens, each having a quantitative efficacy value associated therewith. A treatment regimen may then be selected from the plurality of treatment options based on the efficacy value.

14 Claims, 16 Drawing Sheets

Evolution at 8 Loci

2 Kinetic Loci:
Cell Division and
Apoptotic Rates

6 Resistance Loci:
to each nCS, CS,
and DR Drug

Evolution at 8 Loci

2 Kinetic Loci:
Cell Division and
Apoptotic Rates

6 Resistance Loci:
to each nCS, CS,
and DR Drug

COMPUTATIONAL MODEL, METHOD, AND SYSTEM FOR KINETICALLY-TAILORING MULTI-DRUG CHEMOTHERAPY FOR INDIVIDUALS

I. CLAIM OF PRIORITY IN PROVISIONAL APPLICATION

This application claims priority in provisional application filed on Jan. 7, 2002, entitled "Modeling Multi-drug Chemotherapy: Tumor Control, Resistance, and Toxicity" Ser. No. 60/346,631, by Shea Gardner.

The United States Government has rights in this invention pursuant to Contract No. W-7405-ENG-48 between the United States Department of Energy and the University of California for the operation of Lawrence Livermore National Laboratory.

II. FIELD OF THE INVENTION

The present invention relates to modeling, predicting, and tailoring optimal treatment regimens to individuals with diseases exhibiting evolution of resistance to treatment, such as cancer. More particularly, the present invention relates to computational models, methods, systems, and computer program products for tailoring drug combinations, doses, and schedules based on tumor cell kinetics, and incorporating intra-tumor heterogeneity and evolution of drug resistance, apoptotic rates, and cell division rates.

III. BACKGROUND OF THE INVENTION

Multi-drug chemotherapy has been shown to be a more effective treatment than with a single drug, and research efforts have endeavored to develop methods and models for selecting optimal drug combinations, doses, and schedules likely to be most effective and not excessively toxic. However, heterogeneity in clinical response due to variations in tumor cell structure and cell cycle kinetics remains a formidable challenge, especially for developing optimal treatment regimens among individuals. The many factors that affect responses to chemotherapy, such as rates of cell division, cell death, and the evolution of drug resistance, among others, interact in complex ways. Both biochemical and kinetic resistance affect treatment outcomes (Norton & Simon, 1986). In addition, there is extreme inter-patient and intra-patient heterogeneity in these factors. The evolution of resistance in particular confounds therapeutic attempts and stands as one of the primary obstacles to successful treatment. The speed at which resistance evolves depends on the rates of mutation, division, and death of tumor cells. In addition, treatment efficacy and evolution of resistance depends on the types of drugs and the doses and schedules by which they are applied.

Notwithstanding these and other complexities, individually tailored treatment regimens, and the methods, systems and models for producing such regimens, are beginning to receive greater attention as more information becomes available about specific genes involved in oncogenesis and drug responses, and as methods to measure cell kinetics become feasible to perform in a clinical setting. For example, U.S. patent application Publication No. U.S. 2002/0095258 A1 discloses, in one embodiment, a method and system for recommending optimal treatment protocols for an individual. In another embodiment, a method and system for predicting progression of a biological process in an individual patient under a plurality of protocols is also disclosed. The system model is based on discrete time and requires an unspecified "fitness function" to optimize treatments. And while this publication suggests incorporating data from the clinic (tumor biopsies) in the selection of parameters, the required parameters remains unspecified other than a need to know all the age-specific and time-specific transition probabilities of cells between every phase of the cell cycle, and how each of these probabilities is affected by treatment. And many key limiting factors necessary for realistic biological modeling, such as evolution of drug resistance in response to treatment, and the rate of apoptosis, among others, are not incorporated into the model.

There is therefore a need for a more realistic model and effective method and system for modeling biological systems using tumor cell kinetics and incorporating evolution to predict response to treatment in realistic circumstances. Such tumor cell kinetics would be based on parameters measured from tumor biopsies (e.g. apoptotic index, proliferative fraction, S-phase fraction, cell-cycle time, drug resistance), and thereby enable tailoring of treatment to individuals. Such a model would reduce the number of clinical trials to be performed, as resources could be directed to trials predicted by the model to result in a statistically significant improvement in outcome. Additionally, more robust predictions may be produced before treatments are tried in vivo.

IV. SUMMARY OF THE INVENTION

One aspect of the present invention includes a method for tailoring treatment regimens to individual patients with diseased cells exhibiting evolution of resistance to such treatments, said method comprising the steps of: providing a mathematical model which models rates of population change of proliferating and quiescent diseased cells using cell kinetics and evolution of resistance of the diseased cells, and pharmacokinetic and pharmacodynamic models; obtaining cell kinetic parameters from an individual patient; applying the cell kinetic parameters to the mathematical model to solve for a plurality of treatment regimens, each having a quantitative efficacy value associated therewith; and selecting from one of the treatment regimens based on the efficacy value.

Another aspect of the present invention includes a system for tailoring optimal cancer treatments to individual patients based on tumor cell kinetics, said system comprising: a mathematical model for modeling rates of population change of proliferating and quiescent tumor cells using cell kinetics and evolution of resistance of the tumor cells, and pharmacokinetic and pharmacodynamic models; an input module for receving cell kinetic data obtained from an individual patient; a system processor for applying the cell kinetic data to the mathematical model to solve for a plurality of treatment regimens, each having a quantitative efficacy value associated therewith; and an output module for presenting the plurality of treatment regimens for selection based on the efficacy value.

And another aspect of the present invention includes a computer program product comprising: a computer-readable medium having a computer-readable set of instructions embodied in said medium for enabling a computer system to aid in tailoring optimal cancer treatments to individual patients based on tumor cell kinetics, the set of instructions comprising: a system model code for causing the computer system to mathematically model rates of population change of proliferating and quiescent diseased cells using cell kinetics and evolution of resistance of the diseased cells, and pharmacokinetic and pharmacodynamic models; an input code for causing the computer system to receive tumor cell kinetic parameters obtained from the individual patient; a processing code for causing the computer system to process the mathematical model based on the tumor cell kinetic parameters to produce a plurality of treatment regimens, each having a quantitative efficacy value associated therewith; and an output code for causing the computer system to present the plurality of treatment regimens for selection based on the efficacy value.

V. BRIEF DESCRIPTION OF THE DRAWINGS

The accompanying drawings, which are incorporated into and form a part of the disclosure, are as follows.

Figure 4A:
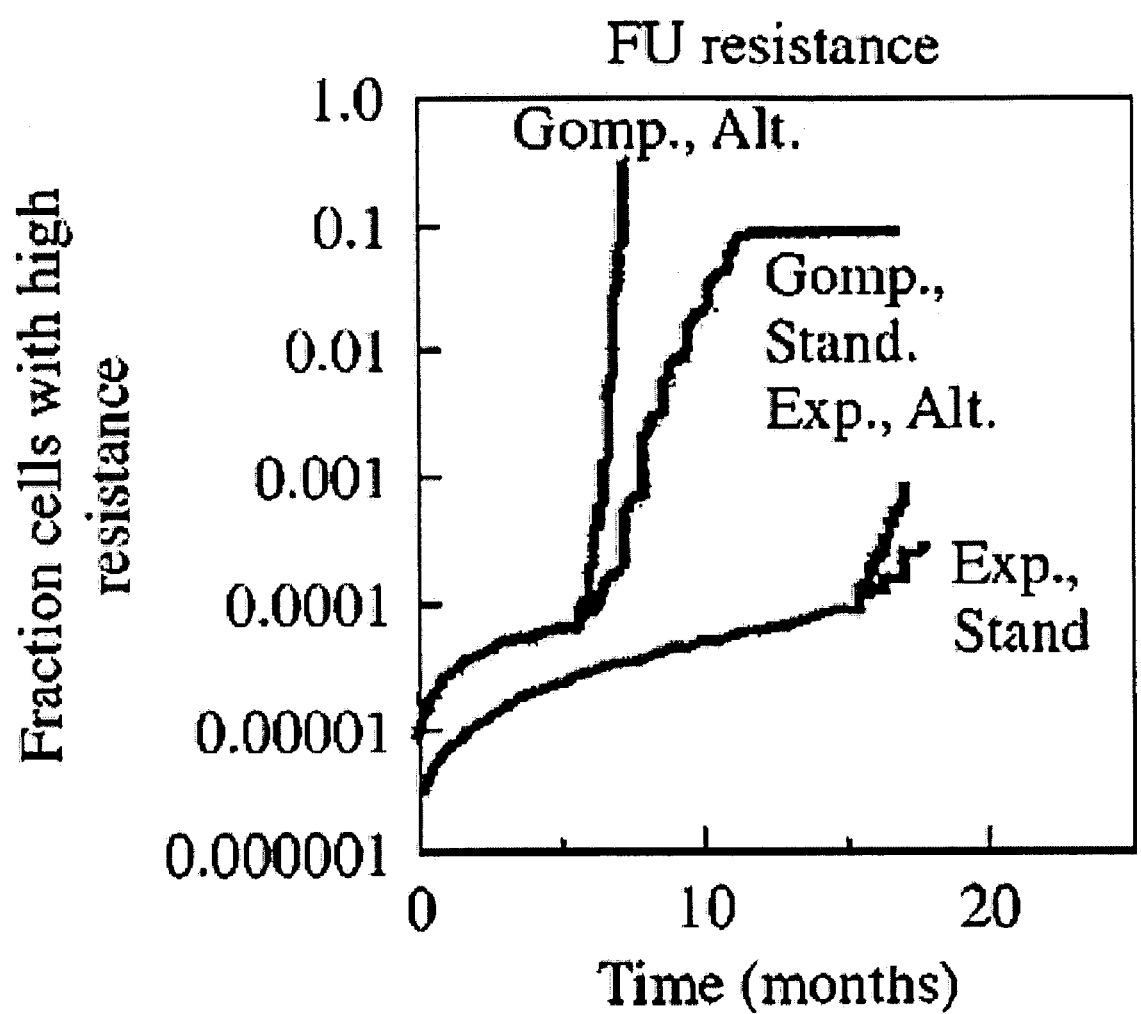
FIG. 4A is a graph of the fraction of tumor cells with the highest level of resistance (r=2) vs. time for the tumors plotted in FIGS. 3A-D to the drug FU.
Figure 4B:
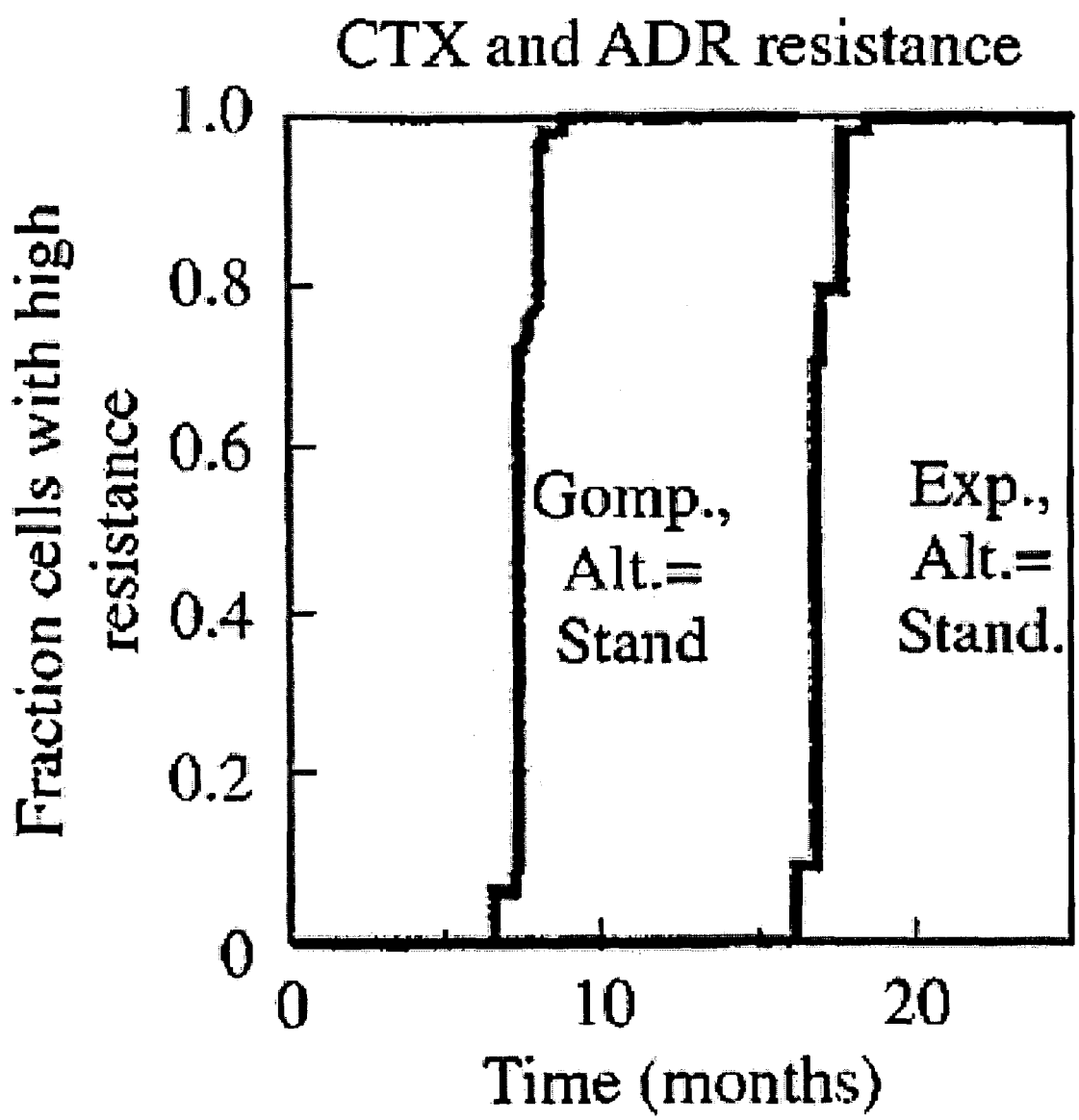
FIG. 4B is a graph of the fraction of tumor cells with the highest level of resistance (r=2) vs. time for the tumors plotted in FIGS. 3A-D to the drugs CTX or ADR.
Figure 4C:
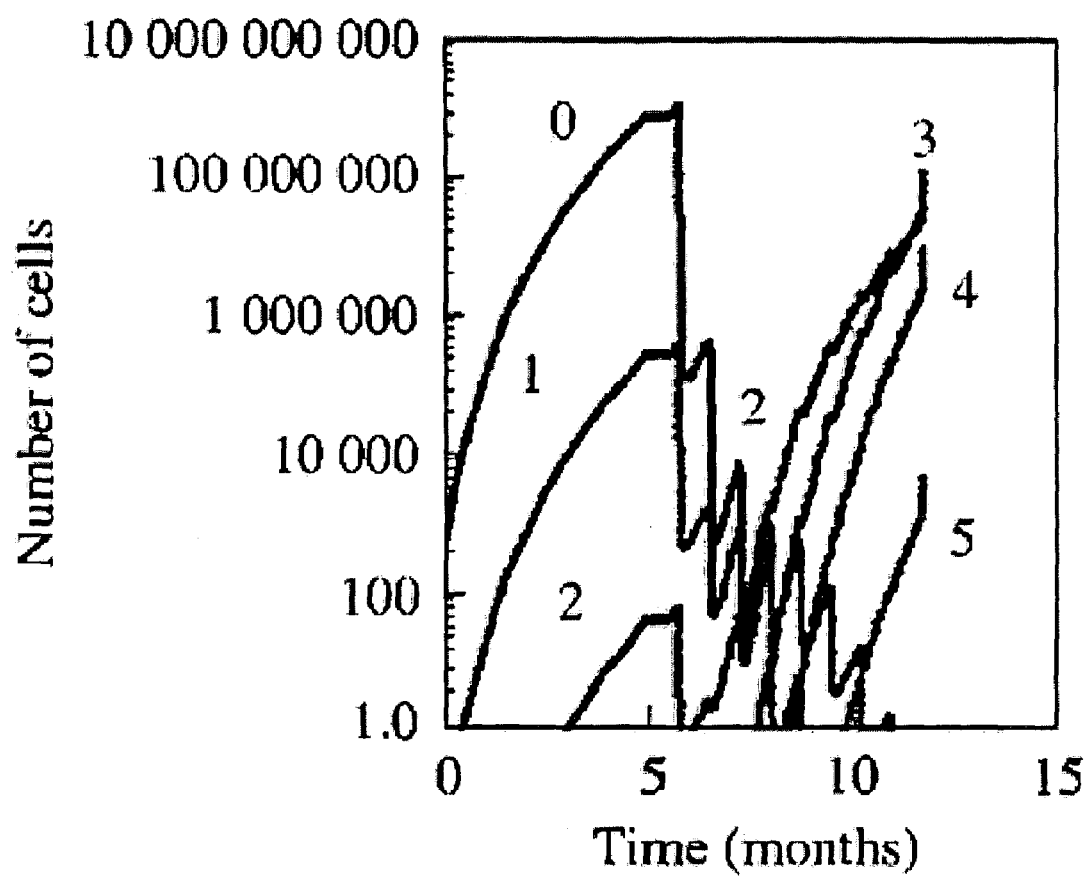
FIG. 4C is a graph of the fraction of cells fully resistant to 0, 1, 2, . . . , 6 drugs for a Gompertzian tumor given the standard schedule shown in FIGS. 3A-D.
Figure 5A:
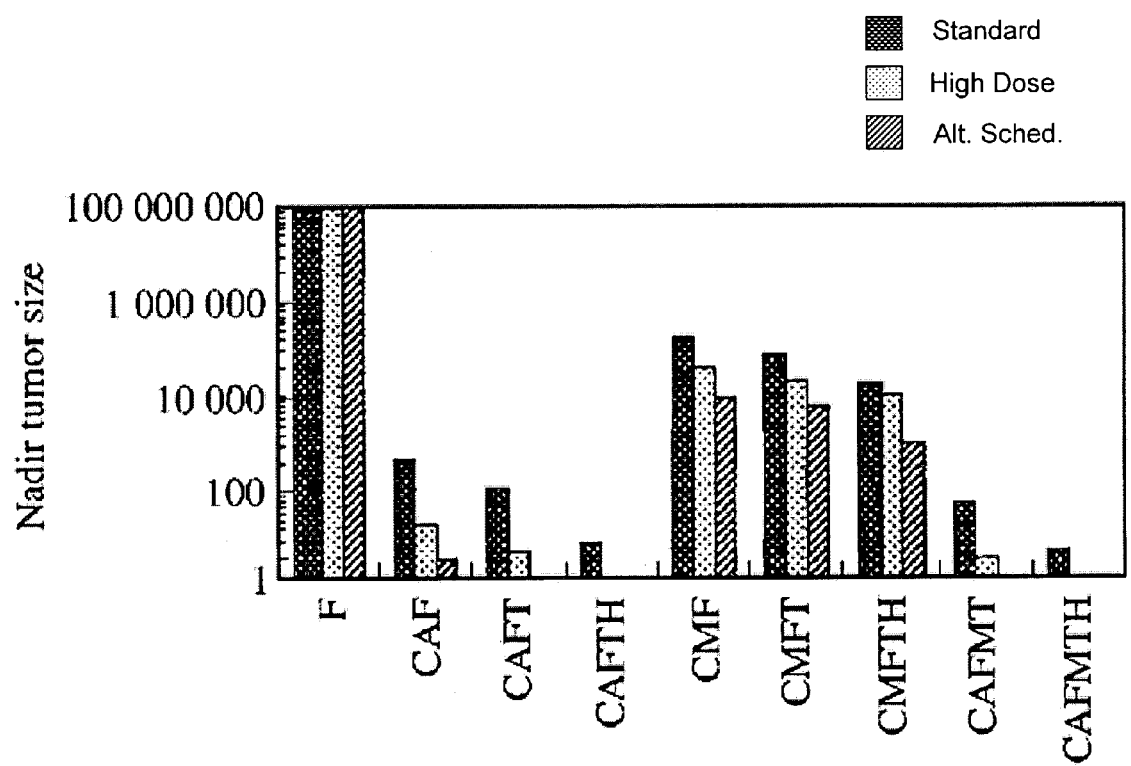

FIG. 5A is a bar graph of the predicted nadir of tumor size for different drug combinations in tumors with the kinetics in FIGS. 3A-4C given at the standard doses and schedules in Table 2, by high-dose therapy in which the dose intensity of each drug is doubled, and by alternate schedule therapy in which the dose intensities are the same as in the standard schedule but the CS drugs FU and MTX are given weekly by CI for 48 hr. Alternate schedule therapy is predicted to be more effective than high-dose therapy. CAF (=FAC) is predicted to be more effective than CMF. Inclusion of the cytostatic drugs TAM and HER to any regimen of cytotoxic drugs is predicted to substantially increase the probability of cure.

Figure 5B:
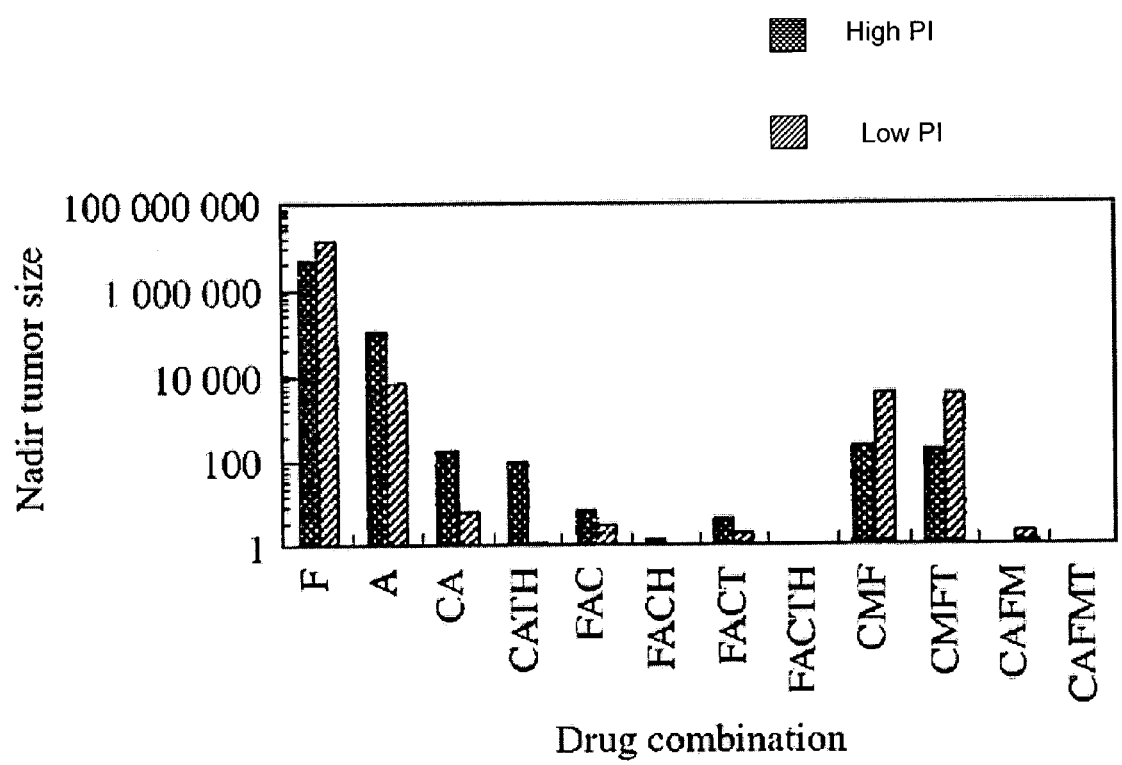

FIG. 5B is a bar graph of the predicted nadir of tumor size for different drug combinations at standard doses and schedules in a &&low-PI tumor" with PI=5%, AI=0.5%, and c=50 hr, and a &&high-PI tumor" with PI=50%, AI=3.5%, and c=30 hr. Regimens with two nCS drugs (ADR and CTX) are more effective in patients with a low PI than with a high PI, while regimens with two CS drugs (FU and MTX) are more effective in patients with a high than with a low PI.

Figure 6A:
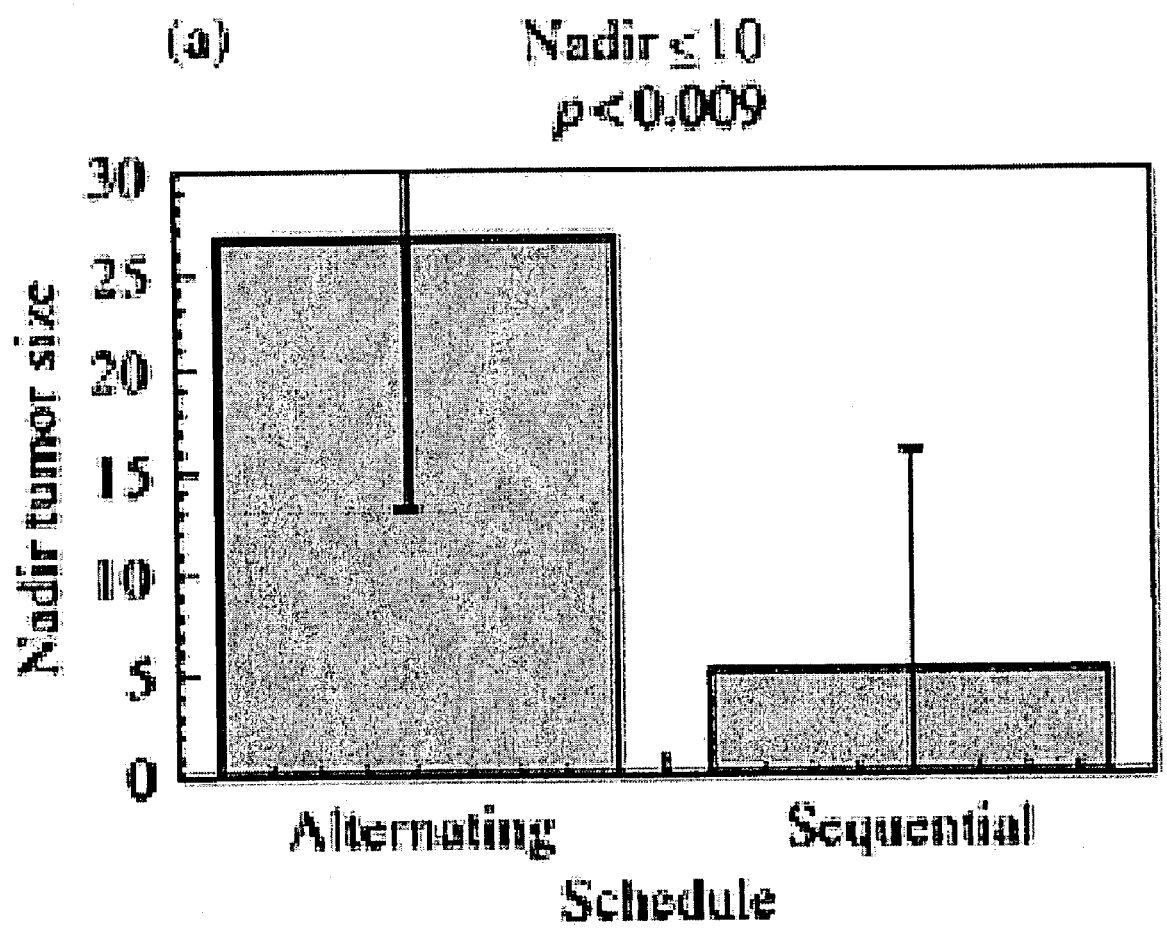

FIG. 6A is a graph of the average nadir tumor size for tumors simulated to model the Silvestrini et al. (2000) and Bonadonna et al. (1995) clinical trial. A comparison of only simulated tumors in which there is a reasonable chance of cure (the nadir tumor size is less than or equal to ten cells) shows that the sequential regimen is predicted to result in a smaller nadir, and thus a higher probability of cure, than the alternating schedule.

Figure 6B:
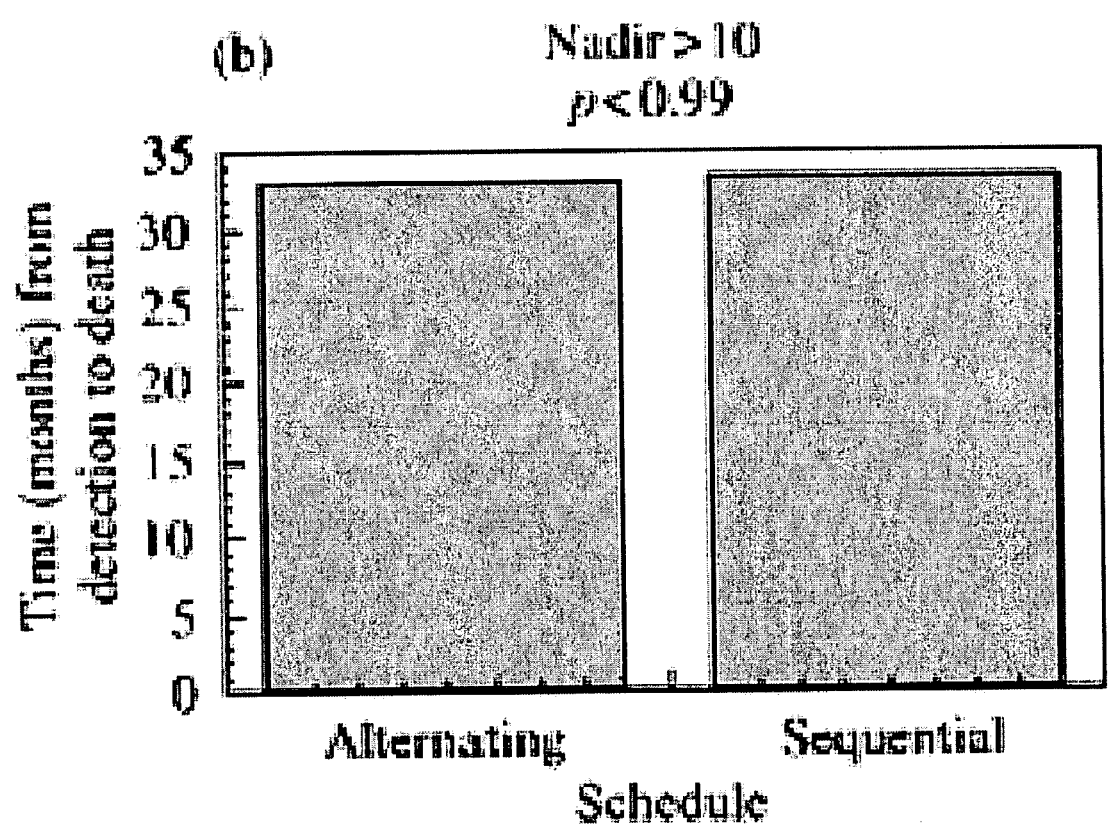

FIG. 6B is a graph associated with FIG. 6A of the time from detection to death.

Figure 7A:
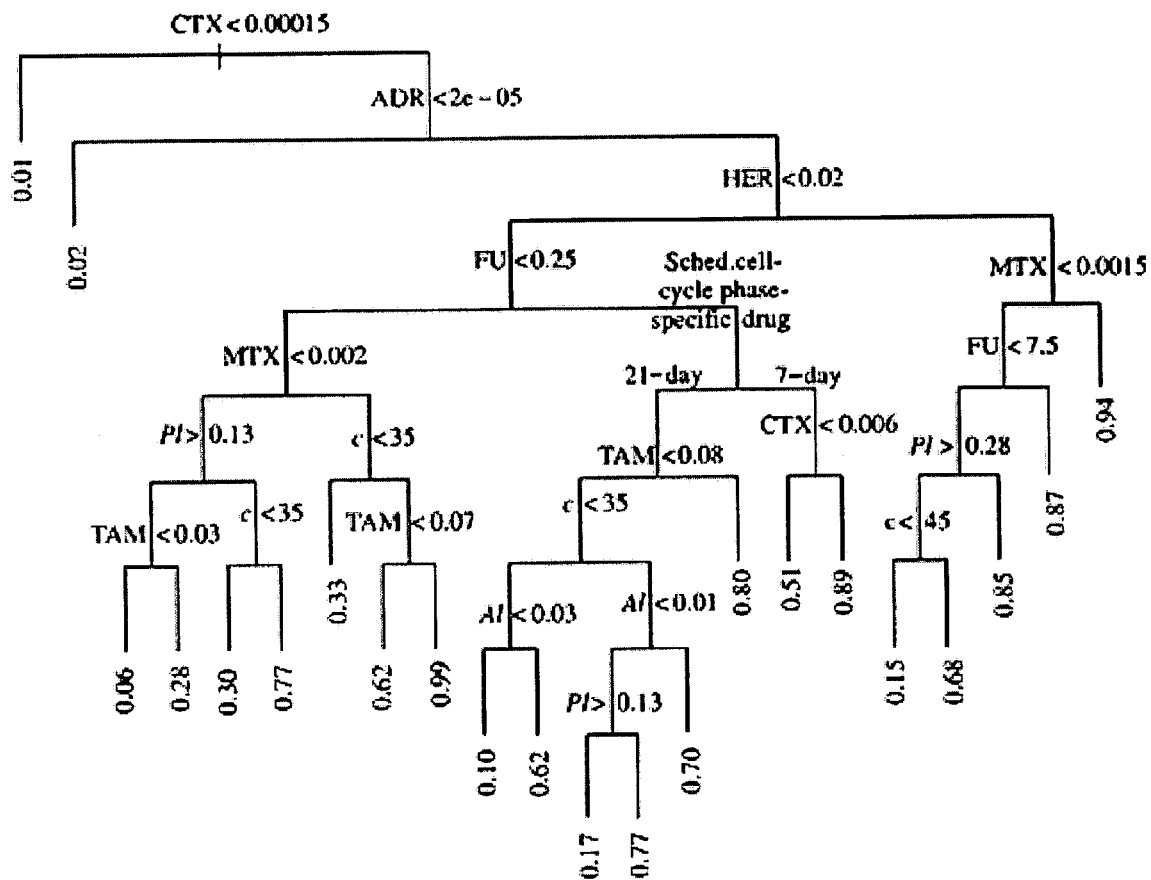

FIG. 7A is a decision tree based on probability of survival and constructed from the simulation of 26,896 tumors. The physician-controlled factors of drug dose and schedule are illustrated in bold, and the tumor-specific factors of AI, PI, and c are in italics. (a) Probability of survival.

Figure 7B:
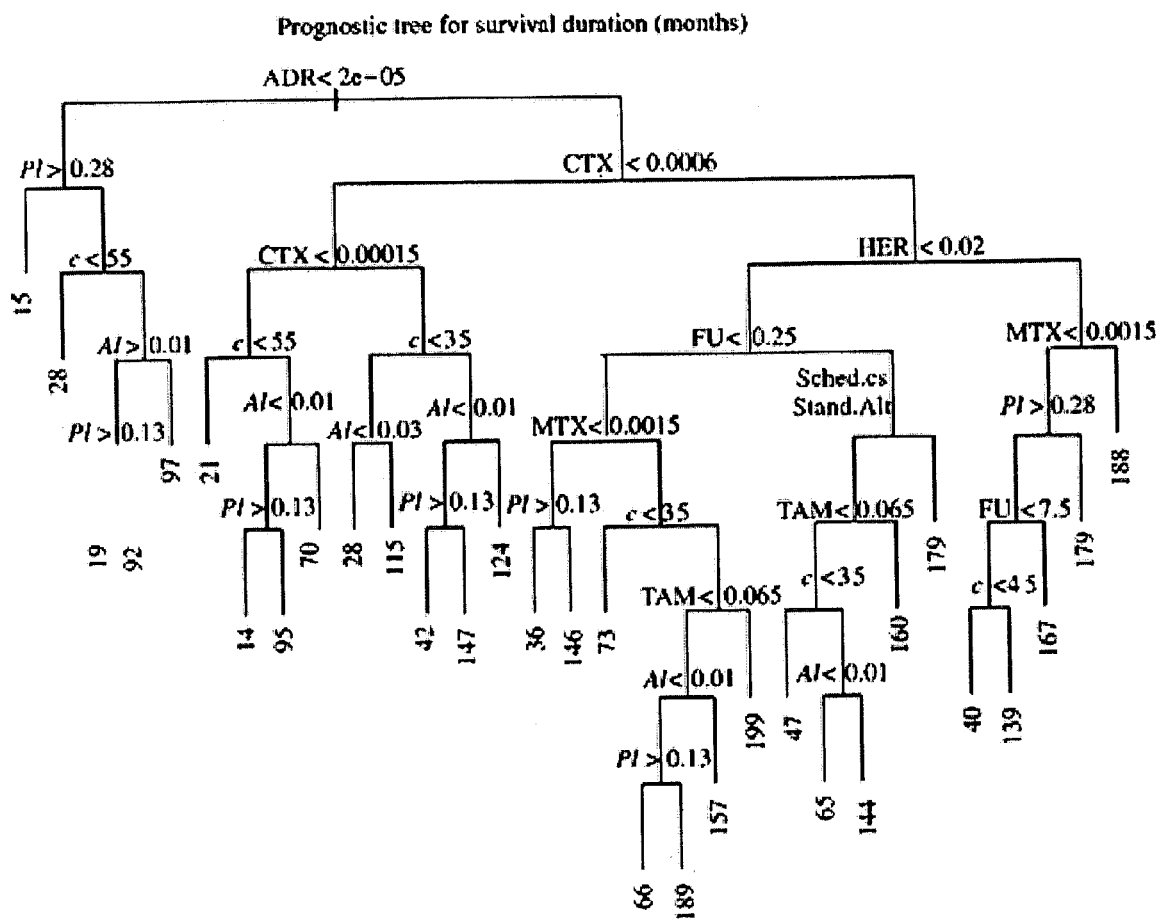

FIG. 7B is a decision tree based on duration in months from tumor detection to patient death and constructued from the same simulation of FIG. 14.

Figure 8:
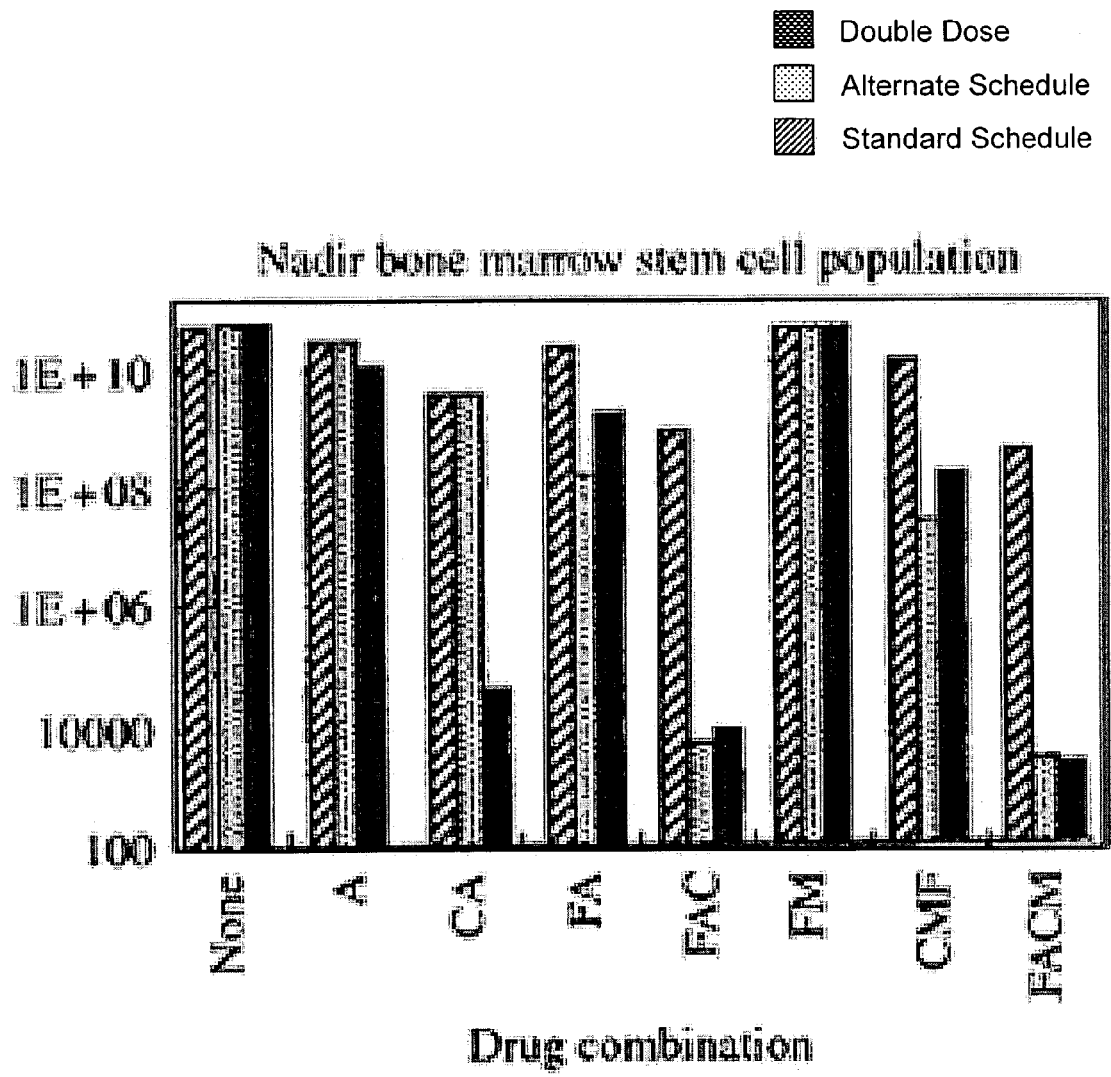

FIG. 8 shows the predicted nadir of bone marrow hematopoietic stem cell numbers in response to different drug combinations applied at the standard schedules in Table 2, at high doses double those in the standard regimen (see text), or by the alternative schedule of weekly FU and MTX by 48 hr CI. Treatments involving CA at high doses are predicted to be very toxic, as are treatments involving FAC with FU at the alternate schedule.

VI. DETAILED DESCRIPTION OF THE PRESENT INVENTION

A computational model of the present invention is disclosed incorporating cell kinetic parameters obtained from tumor biopsies, evolution of cell kinetics, and evolution of resistance of a tumor, among other factors, to more realistically model a biological system, and thereby predict and tailor multi-drug cancer treatments for individuals. The computational (or mathematical) model is therefore considered a kinetically tailored treatment or "KITT" model, which predicts drug combinations, doses, and schedules for an individual patient likely to be effective in reducing (or eliminating) tumor size and prolonging the patient's life. In particular, the KITT model predicts how combination chemotherapy of cell-cycle phase-specific, phase-nonspecific, and cytostatic drugs affects tumor growth and evolution of resistance. The model incorporates intra-tumor heterogeneity and evolution of drug resistance, apoptotic rates, and cell division rates. Evolution of drug resistance is perhaps the primary reason for conventional treatment failure, and is therefore a key component of KITT. Tumor growth may follow an exponential or a Gompertzian trajectory, and drug pharmacodynamic and pharmacokinetic models are used. Predictions depend on the cell kinetics of the tumor and of the toxicity-limiting host tissue. Thus, the KITT model may be used to examine how successful drug combinations, dose intensities, and schedules may differ among individuals based on the contrasting cell kinetic properties of their tumors. The KITT model may be used to compare outcomes for tumors with contrasting cell kinetics as a result of using various drug combinations, dose intensities, and schedules. As will be discussed in detail herein, model results appear to be consistent with published clinical data. While the present discussion describes the method and system used for cancer treatment in particular, the general principles of combination drug therapy discussed may also be used to model treatment of other diseases, such as viral or bacterial infections, in which resistance evolves to treatment (Acar & Goldstein, 1998; Mathe, 1998), as well as to pest control (Carey, 1982;

Gardner et al., 1998). In addition to the combination drugs for chemotherapy, radiation therapy may also be incorporated into the mathematical model.

Additionally, methods and systems are disclosed including and utilizing the core computational model described above, for predicting and tailoring multi-drug cancer treatments for individuals based on tumor cell kinetics, evolution of cell kinetics, and evolution of resistance of a tumor, among others. The system further includes a mathematical model for modeling rates of population change of proliferating and quiescent tumor cells using cell kinetics and evolution of resistance of the tumor cells, and pharmacokinetic and pharmacodynamic models. An input module is provided for receiving cell kinetic data obtained from an individual patient. Additionally, the system includes a processor for applying the cell kinetic data to the mathematical model to solve for a plurality of treatment regimens, each having a quantitative efficacy value associated therewith. And the plurality of treatment regimens are presented for selection, such as on a monitor, or other output module. In the alternative, presentation of the results may be stored on a storage device, for later viewing. It is notable that a treatment regime may be selected based on the quantitative efficacy value, which may be, for example, the probability of survival, or survival duration.

Another aspect of the present invention is a computer program product which includes a computer readable medium, such as any fixed media, including but not limited to hard disk, floppy disk, compact disk, chips, tapes, etc. The computer readable medium includes instructions written in a suitable computer language, such as the C programming language, for enabling a computer to aid in presenting treatment options to a doctor, other health professional, or scientist, for an individual patient. Kinetic parameters, such as those clinically obtained from a patient by a health professional or scientist, are received as input by an input code. The set of instructions also includes a system model code for causing the computer system to mathematically model rates of population change of proliferating and quiescent diseased cells using cell kinetics and evolution of resistance of the diseased cells, and pharmacokinetic and pharmacodynamic models. A processing code is also provided for causing the computer system to process the mathematical model based on the tumor cell kinetic parameters to produce a plurality of treatment regimens, each having a quantitative efficacy value associated therewith; and an output code for causing the computer system to present the plurality of treatment regimens for selection based on the efficacy value.

As used herein and in the claims, the following abbreviations are used: KITT, kinetically tailored treatment; CS, cell-cycle phase-specific cytotoxic; nCS, cell-cycle phase-non-specific cytotoxic; DR, cytostatic; FU or F, 5-fluorouracil; MTX or M, methotrexate; CTX or C, cyclophosphamide; ADR or A, adriamycin=doxorubicin; TAM or T, tamoxifen; HER or H, herceptin; PI, proliferative index, fraction of cells in the proliferating (as opposed to the quiescent) state; SPF, S-phase fraction; AI, apoptotic index, fraction of cells undergoing apoptosis. Results presented and discussed herein are based on parameters characteristic of breast cancer, and the drugs modeled are FU, MTX, CTX, ADR, TAM, and HER.

VI.A. Tumor Dynamics and Evolution

Figure 1:
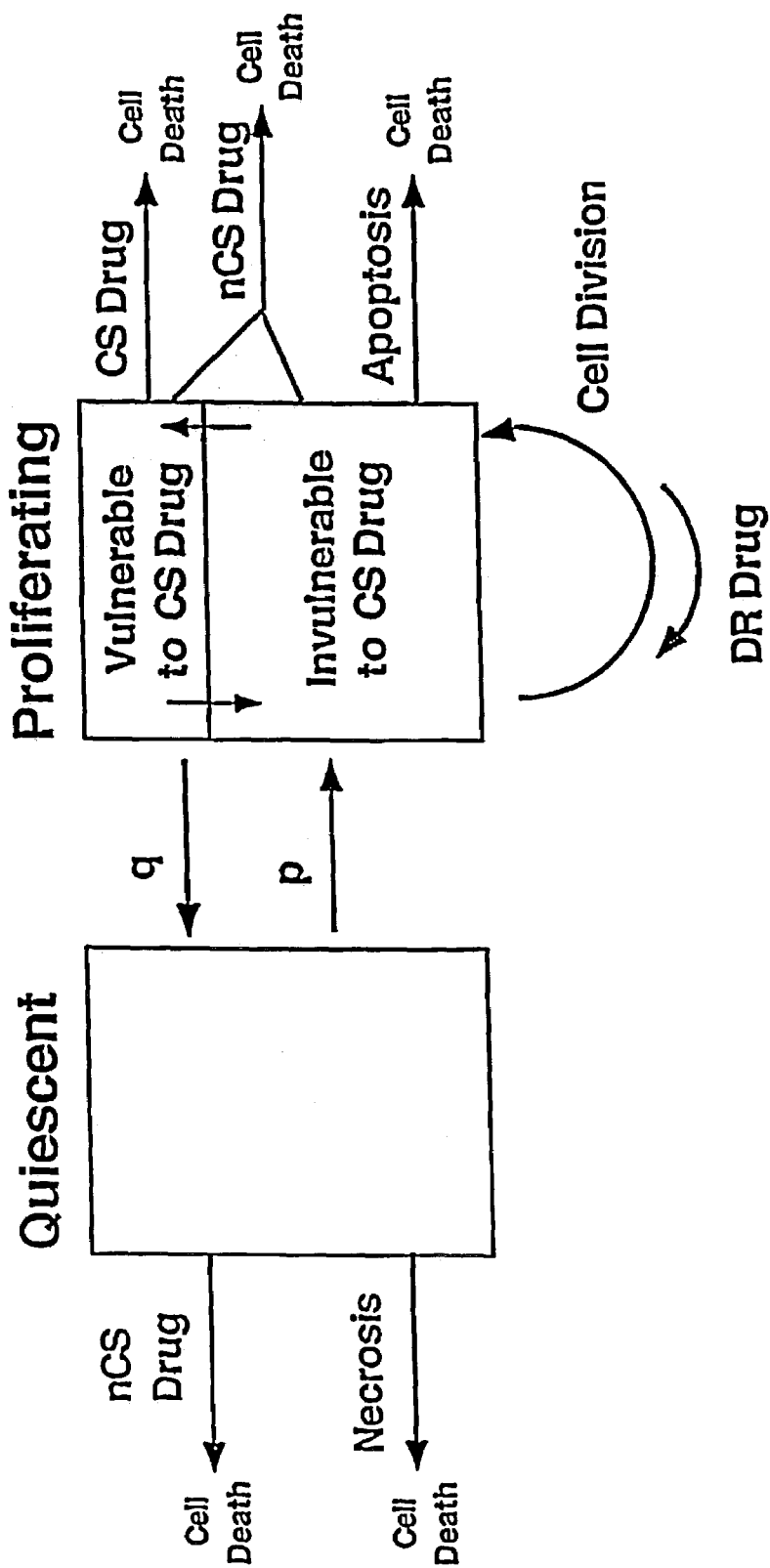
FIG. 1 is a schematic diagram of the basic structure and cellular dynamics of the model of the present invention.
Figure 2:
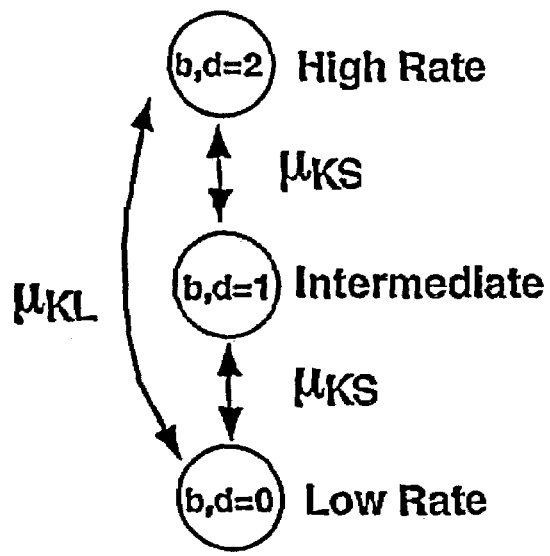
FIG. 2 is a schematic diagram of mutations in the model that generate intra-tumor heterogeneity.
Figure 2:
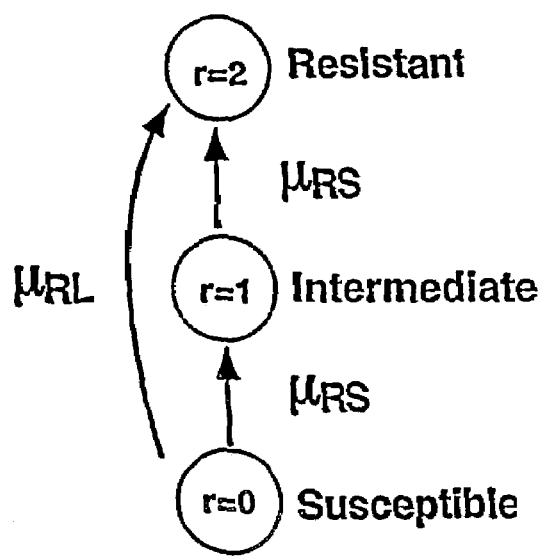

The present invention calculates tumor growth and evolution in response to different treatments. Seven processes operate: (1) cell division; (2) apoptosis, not caused by chemotherapy; (3) cell death caused by chemotherapy, which depends on drug concentration and resistance; (4) mutations conferring drug resistance or affecting rates of cell division and apoptosis; (5) competition between clonal lines; (6) necrosis; and (7) transition of cells between the proliferating and resting states, and vice versa. FIG. 1 shows a diagram of the basic structure and cellular dynamics of the model, in which tumor cells are grouped into two compartments, proliferating and quiescent. Proliferating cells may divide, die via apoptosis, or enter the quiescent state. Proliferating cell division produces susceptible or resistant offspring. They die from natural apoptosis, as well as from CS and nCS drugs, although only a fraction of proliferating cells may be in a vulnerable part of the cell cycle to the CS drug at any time. Quiescent cells may die from necrosis or transfer back to the proliferating state. In addition, nCS drugs may kill cells in the quiescent compartment (van Putten, 1974). nCS drugs kill cells in both the resting and the proliferating states, while CS drugs kill only a fraction of proliferating cells in a particular phase of the cell cycle. DR drugs slow the progression of cells through cell division. FIG. 2 shows a diagram of mutations in the model that generate intra-tumor heterogeneity. Mutations may occur at loci affecting the cell division and apoptotic rates, as well as at six loci each controlling drug resistance to a particular drug. Mutations of large effect occur with probability $\mu_{RL}=\mu_{KL}=10^{-6}$, and those of small effect with probability $\mu_{RS}=\mu_{KS}=10^{-4}$. The clonal evolution of cell division and apoptotic rates and of resistance is superimposed on the compartmental model of cell dynamics. Cells must be classified by both their kinetic status (proliferating or quiescent) as well as their genetic make-up.

In cancer therapy, the evolution of resistance confounds therapeutic attempts and stands as one of the primary obstacles to successful treatment. The speed at which resistance evolves depends on the rates of mutation, division, and death of tumor cells. In addition, treatment efficacy and evolution of resistance depends on the types of drugs and the doses and schedules by which they are applied. One may broadly classify drugs as cell-cycle phase-specific (CS, e.g. FU and MTX), cell-cycle non-specific (nCS, e.g. CTX and ADR), or cytostatic (DR, division reducing, e.g. TAM and HER). Anti-angiogenic compounds and matrix metalloproteinase inhibitors may be other DR drugs (Yip et al., 1999). Not only do these types of drugs have contrasting effects on cellular population dynamics, they are also likely to have different effects on evolution within a tumor. CS drugs, by selectively killing clones with the highest proliferative fractions, may result in the evolution of slower tumor growth (Bottini et al., 1998; Colleoni et al., 1999). nCS drugs, in contrast, may favor clones with high proliferative fractions, because those are the clones with the greatest re-growth between drug applications. Cytostatic (or DR) drugs may slow the evolution of resistance by reducing cell turnover (Lonn et al., 1993). The response to these three general types of drugs, both in terms of the initial response to treatment as well as the subsequent evolution of resistance, depends on the cell kinetics of the tumor. Key cell kinetic features are the proliferative index (PI), the S-phase fraction (SPF), the cell-cycle time of proliferating cells (c), and the apoptotic index (AI).

The model of the present invention is composed of a set of two differential equations, described in Appendix A which is solved using numerical procedures. The differential equations are preferably solved by a computer program product after receiving input data describing cell kinetics, mutation rates, dose response curves and drug pharmacokinetics. Parameters, variables, and functions used in the model equations are defined in Table 1.

TABLE 1

Definitions of parameters, variables and functions

| Variable or Function | Definition (units) |
| --- | --- |
| b | Allele modifying the cell cycle time, assumed to be an integer $0 \leq b \leq b_{max} = 2$. If $b > 0$, then the cell cycle time is shorter than its initial value (hours). |
| $B(b, Z_{DR1}, Z_{DR2})$ | Cell division rate of cells with allele b, exposed to DR drugs 1 and 2, referred to as B (hours$^{-1}$) |
| c | Cell cycle time (hours) |
| d | Allele affecting the cell loss fraction, assumed to be an integer $0 \leq d \leq d_{max}$ (unitless) |
| $d_0$ | Evolved cell loss fraction of cycling cells, expressed as a unitless fraction of the cell division rate |
| $D_a(B, d)$ | Apoptotic rate of cycling cells with birth rate B and apoptotic allele d (hours$^{-1}$) |
| fi | Initial fraction of cycling cells vulnerable to the i$^{th}$ CS drug (e.g. S-phase fraction for an S-phase specific drug) at the start of drug exposure, assuming cells are not synchronized in the cycle at the start of drug exposure (unitless fraction) |
| h | Duration of continuous infusion (hours) |
| k | Probability per unit time of cell death in the proliferating compartment, resulting from a combination of natural apoptosis or drugs (hour$^{-1}$) |
| $\mu_{KL}, \mu_{KS}$ | Mutation rates per cell generation for large effect (i.e. that increase or decrease the cell division or apoptotic fraction to a maximum or minimum in a single mutation) and small effect (i.e. that result in a gradual change in the value of a kinetic allele) kinetic mutations, respectively (mutations cell$^{-1}$ division$^{-1}$) |
| $\mu_{RL}, \mu_{RS}$ | Mutation rates per cell generation for large effect (i.e. that confer complete drug resistance in a single step) and small effect (i.e. that increase resistance, gradually through multiple mutations) resistance mutations, respectively (mutations cell$^{-1}$ division$^{-1}$) |
| $N_x(r_{CS1}, r_{CS2}, r_{nCS1}, r_{nCS2}, r_{DR1}, r_{DR2}, b, d, t)$ | Number of cells which are in the proliferating state (x = P) or the quiescent state (x = Q) with the specified values of the resistance and kinetic alleles at time t (cells). |
| p | Transition rate of cells from the quiescent to the proliferating compartment (hour$^{-1}$) |
| q | Transition rate of cells from the proliferating to the quiescent compartment (hour$^{-1}$) |
| $r_{CSi}, r_{nCSi}, r_{DRi}$ | Allelic values representing the levels of resistance to the i$^{th}$ CS, nCS, or DR drugs, respectively. For simplicity these variables are assumed only to take on integer values $0 \leq r \leq r_{max} = 2$ (per unit concentration, e.g. mg$^{-1}$). |
| $s_{CS}(r, B, f, y, a)$ | Probability per unit time that proliferating cells with resistance r, cell division rate B, and vulnerable fraction f survive a CS drug of concentration y (hour$^{-1}$) |
| $s_{nCS}(r, y, a)$ | Probability per unit time that cells with resistance r survive an nCS drug of concentration y (hour$^{-1}$) |
| u | Interval between the start of successive drug applications (hours) |
| y(t) | Drug concentration at time t (mg). If subscripted, indicates to which drug (the i$^{th}$ CS, nCS, or DR drug) the variable refers. |
| $\bar{y}_i$ | Average dose intensity (amount of drug delivered per unit time) of the i$^{th}$ drug (mg hour$^{-1}$) |
| $Z_{DR}(r, y)$ | Hours by which a DR drug of concentration y slows the cell cycle time of cells with resistance r, referred to as $Z_{DR}$ (hours) |
| λ | Exponential rate of drug elimination (hour$^{-1}$) |
| v | Rate of necrosis of cells in the quiescent compartment (hour$^{-1}$) |

In this model, resistance may evolve either by a single mutation of large effect (e.g. change in a target enzyme), or by small, stepwise increments (e.g. slight modifications of the drug target or detoxification efficiency) (Schimke, 1984). The latter, gradual evolution is consistent with mechanisms of gene amplification, sequential modifications of a single gene, or small changes in a number of genes, each of which confers a degree of resistance. Similarly, mutations that change the rates of cell division and apoptosis from a parent to an offspring cell may occur by mutation of a major monogene or by stepwise, small changes over more than one cell generation (Alitalo, 1985). The probability that a mutation occurs conferring a small, stepwise increase in drug resistance is assumed to be higher than the probability that a mutation occurs conferring a large increase in drug resistance in a single cell generation.

To model the evolution of resistance, the tumor is divided into subpopulations, or clones, based on the genetic constitution of cells. In each cell, the loci $r_{CSi}$, $r_{nCSi}$, and $r_{DRi}$ may take on the allelic values of 0, 1, or 2, indicating the level of resistance of that cell to the i-th CS, nCS and DR drugs, respectively. For the most susceptible cells, r=0. For cells with partial resistance, r =1, and for cells with complete resistance to any dose, r=$r_{max}$=2. Resistance may evolve gradually (e.g. from r=0 to 1) with the probability $\mu_{RS}$, or by a single mutation of large effect (from r=0 to r=$r_{max}$) with probability $\mu_{RL}$. Unless specified otherwise, it is assumed that $\mu_{RL}$=10$^{-6}$ and $\mu_{RS}$=10$^{-4}$, based on the per generation mutation rate (Goldie & Coldman, 1998) and the frequency of gene amplification (Schimke, 1984), respectively. Mutations only increase the level of resistance, and in the absence of the drug there is no selection for decreased levels of resistance. Thus, drug resistance entails no costs in terms of reduced fitness in the absence of the drug. This assumption characterizes a conservative, worst case scenario. Barranco et al. (1988) found two strong pieces of evidence that there is no cost to resistance. First, resistance did not decline in resistant clones cultured for 35 generations in the absence of the drug, and, second, a resistant clone out-competed a susceptible clone even in the absence of a drug. The model also assumes that one selects non-cross-resistant drugs. Finally, in the results described in this paper, a maximum of six drugs may be given, two of any type (i.e. CS, nCS, and DR), although it is straightforward to modify the code to model any number and combination of drugs based on the ideas outlined here. It was decided that approximately six drugs represent the upper limit in cancer chemotherapy considering host toxicity and currently available drugs that do not display cross-resistance and which are active against a particular type of cancer.

The rates of cell division and apoptosis, expressed as a fraction of the rate of cell division, may also evolve. The loci b and d, with allelic values of 0, 1, or 2, indicate the genetic contribution to the rate of cell division and the apoptotic fraction, respectively. Mutations may result in either a decrease or an increase in the allelic values at these kinetic loci. As with resistance evolution, mutations may be of large effect with probability $\mu_{KL}=10^{-6}$ or of small effect with probability $\mu_{KS}=10^{-4}$, based on rates of mutation and gene amplification reported in the literature (Schimke, 1984; Goldie & Coldman, 1998). Considering both the resistance and kinetic loci in the model, there are a total of $r^6_{max}b_{max}d_{max}=3^8=6561$ possible subpopulations, or distinct clones, within the tumor. In addition to the genetic constitution of cells, one must also keep track of whether a cell is proliferating or quiescent. It is assumed that all cells are stem cells capable of further mitoses, since differentiated, end-stage cells cannot contribute to future tumor growth.

Cure is a stochastic event that depends on the minimum tumor size, the nadir, achieved during treatment. The probability of cure is given by the zeroth term of the Poisson distribution, $Pr\{cure\}=\exp(-nadir)$. This probability declines very quickly as the nadir increases above one cell, and is less than $10^{-4}$ for a nadir of only 10 cells. The aim of treatment is to minimize the nadir tumor size.

Surgical tumor resection is modeled as the removal of the oldest 99% of tumor cells, leaving 1% survival of the most recently produced cells which are then exposed to adjuvant chemotherapy. The youngest cells were assumed to survive because they are the most likely to metastasize before the older bulk of tumor is extracted. Unfortunately, the youngest cells that arise after many generations of clonal evolution within a tumor are also more likely than older cells to contain resistant alleles, as well as alleles conferring high rates of cell division and low rates of apoptosis.

Some simplifying assumptions may be made of the KITT model for facilitating computation. It is appreciated, however, that such assumptions are not intended to be limiting and does not operate to preclude the adoption of other assumptions, including counter assumptions. First, dynamics are assumed deterministic, predicting the mean behavior of the population but not fluctuations around the mean. However, cancer is a stochastic process because mutation and the survival of small numbers of cells are a result of random events. In addition, individuals differ in their responses to treatment because of heterogeneity in cell kinetics, mutation rates, variation in tumor size at detection, drug pharmacokinetics, and the ability of the immune system to fight the cancer and to be maintained in the face of exposure to toxic drugs. Secondly, while a spatial component is assumed not present for the KITT model embodiment discussed above, spatial terms characterizing drug diffusion and cell movement may also be employed. In a solid tumor with poor blood perfusion the drug delivery will change from the outer layers to the core. Third, no biochemistry is included in the model, so, for example, biochemical modulation and synergism between FU and MTX are not incorporated. Fourth, the KITT model does not incorporate host response, for example, in terms of immunity and angiogenesis, as Michelson & Leith (1996, and references therein) have done. Unfortunately, models of host responses have not simultaneously examined how resistance evolves. Finally, KITT does not model multi-drug resistance (MDR) as a result of amplification or elevated expression of the P-glycoprotein pump. However, the KITT model may be applied to P-glycoprotein or other forms of MDR by the following slight modification of the methods used here: all drugs to which the MDR mechanism confer resistance should favor resistant alleles at the same locus, instead of at different loci as the model is currently formulated. This is equivalent to saying that resistant alleles at a single locus give a survival advantage in the presence of a number of different types of drugs.

It is notable that KITT overcomes a number of assumptions that have been made in previous models of resistance evolution (reviewed in Michelson & Leith, 1993; Michelson, 1993). For example, the dose response curves used in the present invention is preferably a Gompertzian curve, which empirically fit in vivo measures of tumor growth better than exponential models (Speer et al., 1984; Norton 1988; Spratt et al., 1993; Marusic et al., 1994). This is unlike some models, particularly those with stochastic dynamics (e.g. Day, 1986; Coldman & Goldie, 1987; Goldie & Coldman, 1998) which assume exponential tumor growth. Additionally, KITT models intra-tumor heterogeneity in cell division and cell death rates and the simultaneous evolution of resistance and kinetic rates, unlike other models which model heterogeneity in tumor growth rates over time or between tumors (e.g. Speer et al., 1984; Norton, 1988). Additionally, KITT incorporates quiescence as an important factor, unlike the stochastic models mentioned above which assume that all cells are proliferating. Empirically, the quiescent fraction of a tumor substantially influences prognosis and response to treatment (Gamel et al., 1995; MacGrogan et al., 1996; Silvestrini et al., 1997; Collecchi et al., 1998; Stapleton et al., 1998; Sinicrope et al., 1999). Quiescence is predicted to be an important factor by the KITT and other models (Skipper et al., 1967; Birkhead et al., 1987; Norton & Simon, 1977). And in most models, drug effects occur instantaneously, and all drugs applied in a given regimen are either CS (Hokanson et al., 1986; Birkhead et al., 1987; Gardner, 2000b) or nCS (Coldman & Goldie, 1987; Harnevo & Agur, 1991; Murray, 1995; Panetta, 1997; Gardner, 2000b), but do not consider combinations of drugs of different kinetic types in the same regimen. Most models are limited to at most two drugs in any regimen. Although in many cases the authors indicate that a "drug" may actually be a combination of drugs, a single mutation can confer resistance to that combination, and all drugs in that combination function with the same pharmacokinetics and pharmacodynamics (i.e. CS, nCS, or cytostatic), so the combination essentially behaves as a single drug. Cytostatic drugs have rarely been incorporated (see Day, 2000). In reality, the drug schedule, method of administration (continuous infusion or IV bolus), pharmacokinetics, cell-cycle phase specificity, and cytostatic action all affect levels of cell kill and the rate of evolution of resistance, and are incorporated into KITT. Moreover, KITT allows resistance to evolve independently and simultaneously to many drugs, each with its own characteristic pharmacokinetics and pharmacodynamics. In addition, most models assume log-linear cell kill. While dose response may be log-linear over a certain range for nCS drugs, it is not log-linear across a wide range for either CS or nCS drugs, and cell kill depends critically on the duration of exposure, both of which were demonstrated empirically by Levasseur et al. (1998). A dose response model that better describes these observations (Gardner, 2000a) is used in KITT.

The majority of chemotherapy resistance models assume that cells are either fully susceptible or fully resistant with high levels of resistance appearing in a single cell generation. While this may occur in some cases, resistance may also evolve in a stepwise fashion via processes of gene amplification, sequential modifications of a gene, or polygenic selection (Schimke, 1984). The KITT model allows for either pattern of sudden, single-step or gradual, multi-step escalation in resistance. It also incorporates dose response curves that allow for partial as well as high levels of resistance depending on the dose. The shape of the dose response curve for a given clone depends on the alleles present. Thus, KITT allows for both induced resistance, in which resistance is dose-dependent, and acquired resistance, in which resistance results from mutations that occur independent of the dose applied, concepts discussed by Panetta (1997). In reality, the distinction between acquired and induced resistance may be moot: in cell culture experiments in which colony survival is measured across a range of doses for different cell lines, variation in dose response curves can be attributed to different mutations among cell lines, and therefore survival depends on both dose and random mutations (O'Conner et al., 1997).

VI.B. Cell Division

The baseline cell-cycle time is denoted by the variable c. Mutations resulting in an increase in the value at the b locus accelerate the progression of cells through the cycle. DR drugs do the reverse; the i-th DR drug slows the cell cycle by an amount $Z_{DRi}$ calculated from a dose response curve, given in Appendix C. The birth rate $B(b, Z_{DR1}, Z_{DR2})$ of a cell with a given value of b (which may differ among cells within a tumor) is the reciprocal of the cell-cycle time, given by $$B(b, Z_{DR1}, Z_{DR2}) = 1/(c - 3b + Z_{DR1} + Z_{DR2}). \quad (1)$$

$B(b, Z_{DR1}, Z_{DR2})$ is denoted by B unless the indexing values are necessary for clarity. The factor 3 in equation (1) means that a mutation which increases the allelic value of b by 1 decreases the cell-cycle time by 3 h. The cell-cycle time in tumors typically ranges from 30 to 60 hrs (Steel, 1977; Baker et al., 1995; Begg, 1997; Panetta, 1997).

VI.C. Apoptosis

Studies have found rates of apoptosis and cell proliferation to be positively correlated (Höckel et al., 1999; Lipponen, 1999; Matsushima et al., 1999). Thus, the rate of apoptosis Da of proliferating cells from natural causes, not induced by drugs, is assumed to be linearly related to the rate of cell division B, following $$Da(B, d) = (d_0 + 0.3d)B, \quad (2)$$

where d=0, 1, or 2 represents different alleles and thus genetic heterogeneity within a tumor (Meyn et al., 1993). The rate of apoptosis $D_a(B, d)$ increases with the rate B of mitosis. However, selection on tumor growth may simultaneously favor an increase in b (and thus the rate of cell division) and a decline in d (and thus the rate of apoptosis). Let $D_a$ denote $D_a(B, d)$. Apoptotic indices (AI: the fraction of apoptosing cells out of the total cells scored) range between 0.1 and 4% (Höckel et al., 1999; Matsushima et al., 1999; Xie et al., 1999) for a variety of types of cancer. Assuming that apoptotic cells do not accumulate and instead are absorbed in a matter of minutes to hours, AI provides an estimate of $D_a$. Rates of cell loss are sometimes expressed as a fraction of the rate of cell division, called the cell loss factor, and estimated to be 29-97% (Steel, 1977; Meyer, 1989; Haustermans et al., 1999). If d=0, then the cell loss factor in equation (2) is $d_0 = AI/B = c_{evolved}]AI$. For a cell-cycle time of 48 hr (B=0.021and an apoptotic rate of $D_a = 0.5\%$ hr$^{-1}$, with d=0, the cell loss is $d_0 = 24\%$. This is considered to be a tumor with a low rate of apoptosis. For a moderate AI of 1.67% with the same cell-cycle time, the cell loss factor is $d_0 = 80\%$ when d=0.

Initial runs of the program revealed that the allele d governing the apoptotic rate evolves to fixation at the minimum possible value early in tumor growth (e.g. for typical parameters, a year before tumor detection and 6 months before the evolution of rapid cell division rates). Therefore, d was set identically to zero, so $D_a(B) = d_0 B$ throughout tumor growth. That tumor cells experience strong selection for low apoptotic rates very early in tumor development, months before alleles at any other loci evolve to fixation, is consistent with in vivo (Höckel et al., 1999) and in vitro (Kim et al., 1997) evidence that mutations lowering the rates of apoptosis occur early in oncogenesis. Initial runs of the model predicting that selection favors clones with low rates of apoptosis regardless of the combination of drugs which is applied are also consistent with empirical observations that the expression of Bcl-2 proteins, which inhibit apoptosis, were not differentially affected by contrasting drug combinations (Diadone et al., 1995).

VI.D. Quiescence

Tumor growth may follow either an exponential or a Gompertzian trajectory. Well vascularized tumors, cancers of the blood, and micrometastases may grow exponentially. In many human tumors, growth is exponential over the period of observation (Haustermans et al., 1999). Solid tumors with poor blood perfusion, however, adhere more closely to Gompertzian growth (Speer et al., 1984; Norton, 1988; Spratt et al., 1993; Marusic et al., 1994). For exponential growth, the transition rate $q_{exp}$ from the proliferating to the quiescent compartment remains constant, independent of tumor size N(t) at time t. For Gompertzian growth (in some cases it is only approximately Gompertzian) (Gyllenberg & Webb, 1989), $$q_{gomp}(t) = q_{exp} \log_e(N(t))/\log_e(N(t_{see})). \quad (3)$$

Thus, the transition rate to the quiescent compartment increases as the tumor becomes larger and declines when drugs or surgery reduce tumor size, resulting in a higher proliferative fraction, and thus faster growth, in smaller than in larger tumors. $N(t_{see})$ is the tumor size at detection, and the denominator $\log_e(N(t_{see}))$ in equation (3) is a constant of proportionality that makes the transition rate $q_{gomp}(t_{see}) = q_{exp}$ when the tumor is detected.

The transition rate $q_{gomp}(t_{see})=q_{exp}$ can be calculated from the PI, AI, and cell-cycle time c, although some assumptions are necessary about how long cells spend in the quiescent compartment and the rate of necrosis. Based on other studies (Killmann, 1968; Lord, 1997; Papayannopoulou et al., 2000; Birkhead et al., 1987; Panetta, 1997), for many of the analyses here it is assumed that the transition rate from the quiescent to the proliferating compartment is $p=\frac{1}{20}$ day$^{-1}$ and that the rate of necrosis from the quiescent compartment is $v=\frac{1}{100}$ day$^{-1}$. This value for the rate of necrosis results in a ratio of necrotic to living tumor tissue that is approximately 0.1-0.5 based on in vivo measures of the necrotic fraction given by Leith & Michelson (1994). The affect of varying these parameters is also addressed.

VI.E. Cytotoxicity of CS and nCS Drugs

Survival probabilities are calculated using the dose response relationships of the exponential kill (EK) model described in Gardner (2000a) and summarized in Appendix C. Survival depends on the time-dependent drug concentration at the site of action, the level of drug resistance, and, for a CS drug, the fraction f of proliferating cells initially in the vulnerable part of the cell cycle (e.g. S-phase) and the cell-cycle time. There are two alternative methods to estimate f for an S-phase-specific drug:

$$f=(\text{time spent in S-phase})/(\text{cell-cycle time of proliferating cells}) \text{ (time measure)} \quad (4a)$$

or $$f=SPF/PI \text{ (number of cells measure)}. \quad (4b)$$

For drugs specific to other phases, f can be computed in a similar manner based either on a time measure or a number measure of cells. Both FU and MTX are S-phase-specific. The ratio of SPF/PI is approximately f=0.4 for typical breast cancers (Gasparini et al., 1991; Collecchi et al., 1998) and was the value used in these calculations.

VI.F. Pharmacokinetic Model of Time-Dependent Drug Concentration

In vivo, drug concentration will likely vary over time. One may use detailed theoretical or empirical pharmacokinetic descriptions of time-dependent drug concentration y(t) at the site of action. For illustrative purposes, this paper uses a simple, one-compartment model with continuous infusion (CI). Equations are presented in Appendix D. The pharmacodynamic model presented here may be combined with other programs specifically designed to predict the pharmacokinetic distribution of drugs in different tissues or with empirical measurements taken directly from patients. Because drug metabolism differs among patients and in some cases can be predicted by genetic analyses, incorporating predictions of individual variation in drug concentration at the site of the tumor is recommended. Drug half-lives and doses are given in Table 2. The doses are scaled so that the dose response parameter a=1 mg$^{-1}$ m2 hr, as described in Appendix C.

A tumor is detected when it reaches a size of $10^9$ cells (approximately a cubic centimeter, Norton, 1988) at time $t_{see}$, and chemotherapy begins. If the tumor is not cured, then the program calculates tumor growth until it reaches a lethal size of $N_L=10^{12}$ cells (approximately 11). The predicted nadir of tumor size should correlate with clinical response rates, and the survival time should correlate with the time to patient death. Chemotherapy continues for 6 months according to the schedule in Table 2 or alternative schedules that will be specified. High-dose therapy is also modeled in which drug dose intensities are twice those in the standard regimens.

TABLE 2

Features of drugs modeled

| Drug | Standard Schedule | Standard Dose Intensity | Plasma Half-life (h) | Scaled dose intensity so that scaling factor a = 1.[c] |
|---|---|---|---|---|
| 5-Fluorouracil | I.V.[a] every 21 days | 600 mg/m$^2$/21 d | 0.3[d] | 5 |
| Methotrexate | I.V. every 21 days | 40 mg/m$^2$/21 d | 8[d] | 0.005 |
| Cyclophosphamide | I.V. every 21 days | 600 mg/m$^2$/21 d | 4[d] | 0.0009 |
| Doxorubicin | I.V. every 21 days | 50 mg/m$^2$/21 d | 25[d] | 0.00012 |
| Tamoxifen | Orally[b], daily | 20 mg/d | 10[e] | 0.01 |
| Herceptin | 30 minute CI, weekly | 2 mg/kg/7 d | 144[f] | 0.01 |

[a]I.V.; Intravascular bolus, modeled as an infusion of 0.1 hours in Eq. D1.
[b]Orally; modeled as an infusion for 2 hours.
[c]See Appendix C for explanation of how these values were selected.
[d]Chabner 1993
[e]http://www.bccancer.bc.ca/cdm/monographs/tamoxifen.shtml
[f]Goldenberg 1999

VI.G Test of the Model Using Published Data

Bonadonna et al. (1995) and Silvestrini et al. (2000) report results of a clinical trial in adjuvant breast cancer in which 403 patients with more than three positive axillary nodes were given cyclophosphamide, methotrexate, 5-fluorouracil (CMF) and doxorubicin (ADR) according to two alternative schedules, holding the doses constant. In the sequential schedule, four treatments of ADR were followed by eight of CMF. In the alternating schedule, two treatments of CMF were followed by one of ADR, and this was repeated four times. All drugs were injected by bolus and treatments were given every 21 days. They concluded that the sequential regimen resulted in higher disease-free survival and overall survival than the alternating schedule, but only for patients whose tumors had low rates of proliferation, that is, [3H]thymidine labeling indices (TLI) on tumor specimens obtained at diagnostic surgery of less than 5%.

To use these results to test the model, first the mathematical model simulated the growth of 122 hypothetical tumors if each tumor were treated by the alternating and by the sequential regimens. The drug pharmacokinetic model incorporated the drug schedules exactly as they were given in the trials: by bolus every 21 days. Tumor parameters for each tumor uniformly spanned the following ranges, based on measurements given in Silvestrini et al. (2000) and published empirical measurements for breast cancer (Steel, 1977; Baker et al., 1995; Begg, 1997; Panetta, 1997): AI, 0.1-1.9%; PI, 3-15%; c, 30-50 hr, $\mu_{RS}=\mu KS10^{-5}-10^{-4}$, $\mu_{RL}=\mu_{KL}=10^{-7}-10^{-6}$. The nadir of tumor size and the duration of patient survival from the time of tumor detection were tabulated. Patients were separated into two groups: those with a conceivable chance of cure with a nadir of 10 or fewer cells for either the sequential or the alternating regimen, and those in which the chance of cure was negligible, with a nadir greater than 10 cells under treatment with both the sequential and the alternating regimens. The mean nadir tumor size was computed for the group with a nadir of 10 or fewer cells, and the mean duration of survival from detection to death was calculated for the group with a nadir greater than 10 cells. The mean PI was calculated for each group.

VI.H Simulations Across A Range of Parameter Values

A total of 26 896 tumors were simulated, requiring the massive parallel processing power of the ASCI Blue supercomputer at Lawrence Livermore National Laboratory. Tumor parameters uniformly spanned the following ranges, based on published empirical measurements for a number of different types of cancer (Steel, 1977; Baker et al., 1995; Begg, 1997; Panetta, 1997): AI, 0.5-3.5%; PI, 5-50%; c, 30-60 hr, 1/(24v)=30-170 days, 1/(24p)=10-30 days. The nadir of tumor size and the duration of patient survival were recorded for treatment with each possible combination of 0 to 6 drugs given according to either the standard schedule in Table 2 or the alternate schedule with CS drugs weekly by 48-hr CI. Drugs were given at a range of doses from zero up to the following: FU, 15 mg$^{-1}$ m$^2$ hr; MTX, 0.005 mg$^{-1}$ m$^2$ hr; CTX, 0.0009 mg$^{-1}$ m$^2$ hr; ADR, 0.00012 mg$^{-1}$ m$^2$ hr; TAM, 0.12 mg$^{-1}$ hr; HER, 0.03 mg$^{-1}$ kg hr. Tumor growth was assumed to follow a Gompertzian trajectory. Some of the parameter combinations did not result in tumor inception and were omitted. Parameter combinations were identified with a prognosis of survival if the nadir tumor size was less than or equal to 10 cells and with a prognosis of death otherwise, yielding a total of 17% survivors. Results using a cutoff of a nadir of 1 cell yielded similar results in statistical analyses of key factors affecting survival, but resulted in only 10% survivors. For those patients presumed cured (nadir) 10 cells), the survival duration was set to a maximum of 200 months. Using the part algorithm in Splus, regression trees were constructed to identify the key parameters affecting the probability of survival and survival duration. The parameter determining the level of tree pruning in the algorithm rpart used for the plots was selected to be cp=0.004-0.006 to achieve a balance of classification precision and graphical clarity.

VI.I. Toxicity

Measures of toxicity to the host are modeled in several ways so that alternative treatment protocols can be compared in terms of both tumor control and host toxicity, i.e. the system may be utilized to compare chemotherapy protocols using several measures of toxicity. A physician may evaluate the importance of toxicity vs. tumor cell kill differently depending on the health and prognosis of the individual patient. In some patients, the aim of treatment may be palliation with minimum toxicity, while in others it may be cure despite higher toxicity. The three measures of toxicity are: the relative average dose intensity, peak plasma drug concentrations, and the nadir of the bone marrow (hematopoietic) stem cell population.

The relative average dose intensity is calculated according to the following procedure, described in (Hryniuk, 1987): (1) the dose intensity of each drug in a given regimen is transformed into a decimal fraction of the same quantity at the standard doses described above using all six drugs; (2) these fractions for each drug are averaged to yield a single number, the average relative dose intensity.

Bone marrow stem cell dynamics are predicted using a simplified version of the model for tumor growth, with parameters for bone marrow stem cell kinetics replacing those for tumor cells: c=24 hr (Tannock, 1978; Baker et al., 1995); AI=2.0% (Callera & Falcao, 1997; Lee et al., 1997); PI at detection=30% (Lord, 1997) v=φ hr$^{-1}$; N$_{BM}$(t=0)=5] 1010 is the number of bone marrow stem cells at time 0 (Hofer et al., 1995). The hematopoietic stem cells are assumed to have mutation rates of zero which means that resistance and cell kinetics do not evolve. Their growth dynamics follow Gompertzian dynamics, based on empirical studies showing that the PI increases if stem cell numbers are depleted (Lord, 1997). Because there are few data regarding how long hematopoietic stem cells spend in the quiescent state, two alternative values of 4 days (p=1/96 hr$_{-1}$) or 14 days (p=1/336 hr$_{-1}$) (Killmann, 1968; Lord, 1997; Papayannopoulou et al., 2000). The parameter f is estimated to be 0.4 based on a PI of 30% and an SPF of 12% (Danova et al., 1996). Because TAM and HER specifically target tumor cells, and because myelosuppression is not a major toxicity for either drug, it is assumed that these two drugs do not have cytostatic effects on the bone marrow.

VI.J. Results

Several general predications result from the KITT model. One key prediction is that including cytostatic drugs like tamoxifen and herceptin during treatment with cytotoxic drugs substantially increases the probability of cure and prolongs patient life. Results also suggest that altering drug scheduling may be more effective but not more toxic than dose escalation. CAF chemotherapy (cyclophosphamide, adriamycin, and 5-fluorouracil) is predicted to be more effective than CMF (cyclophosphamide, methotrexate, and 5-fluorouracil). KITT also suggests that tumors with a high proliferative index (PI) may respond better to drug combinations incorporating two cell-cycle phase-specific drugs than do tumors with a low PI. Tumors with a low PI, in contrast, are predicted to respond better to regimens involving two cell-cycle phase-non-specific drugs than do tumors with a high PI. These predictions are borne out by clinical trial results published in the literature, which are discussed. The results presented herein are based on parameters characteristic of breast cancer, and the drugs modeled are 5-fluorouracil (FU or F when named in combination with other drugs), methotrexate (MTX or M), cyclophosphamide (CTX or C), adriamycin (doxorubicin, ADR or A), tamoxifen (TAM or T), and herceptin (HER or H).

Simulated predictions of the model match well with results from a clinical trial by Silvestrini et al. (2000. *Int. J. Cancer* 87, 405). The results of simulating the growth of 26 896 tumors are used to construct a decision tree for prognosis to identify the key tumor and treatment variables.

VI.J.1 Timecourse of Tumor Growth

Figure 3A:
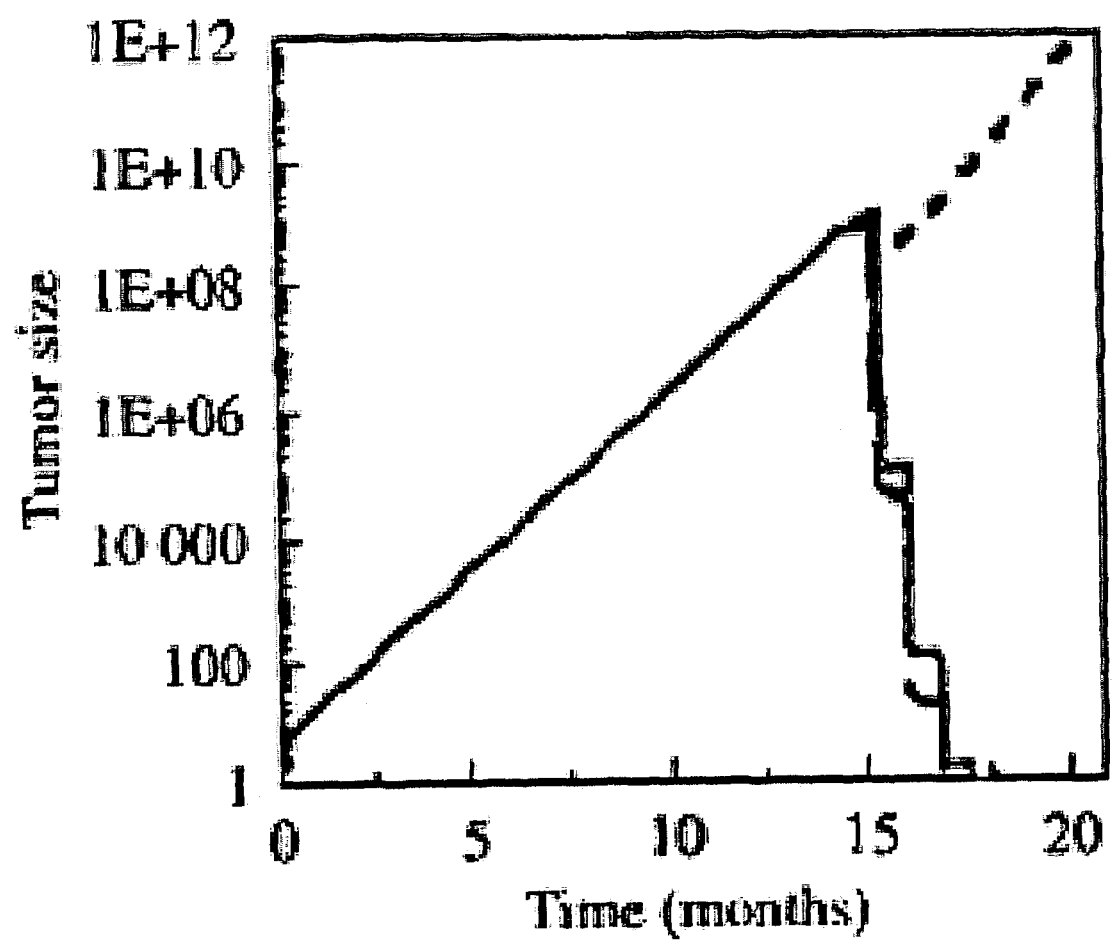
FIG. 3A is a graph of tumor size vs. time in a sample aggressive breast tumor (PI=14%, c=31-37 hr, and AI=0.6%) with no treatment, with a regimen of CAFT given according to the standard schedule specified in Table 2, for exponential growth. (----) No chemotherapy; (-) standard schedule; (--) alternate schedule.
Figure 3B:
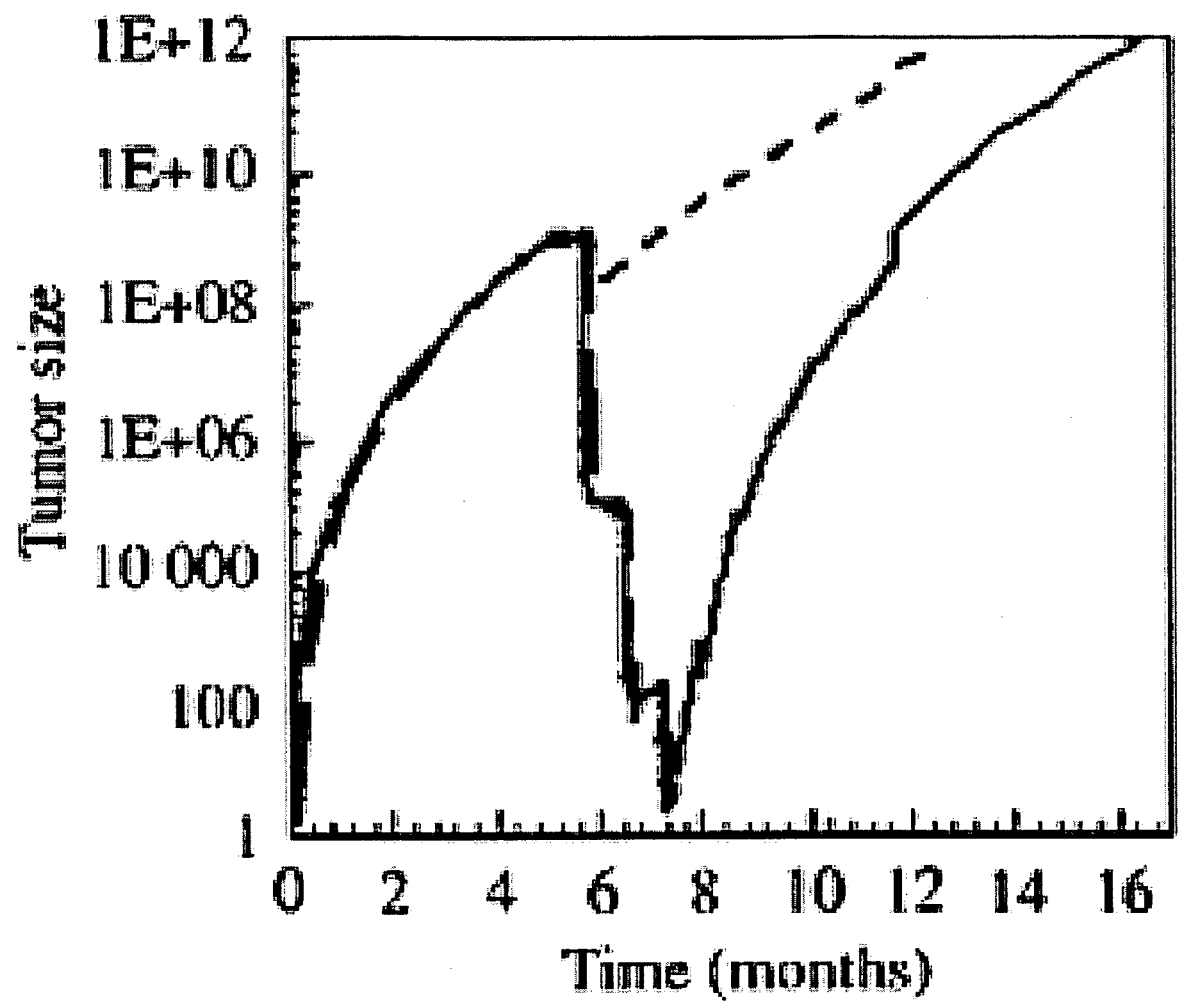
FIG. 3B is a graph of tumor size vs. time in the same sample aggressive breast tumor of FIG. 3, but for Gompertzian growth. (----) No chemotherapy; (-) standard schedule; (--) alternate schedule.
Figure 3C:
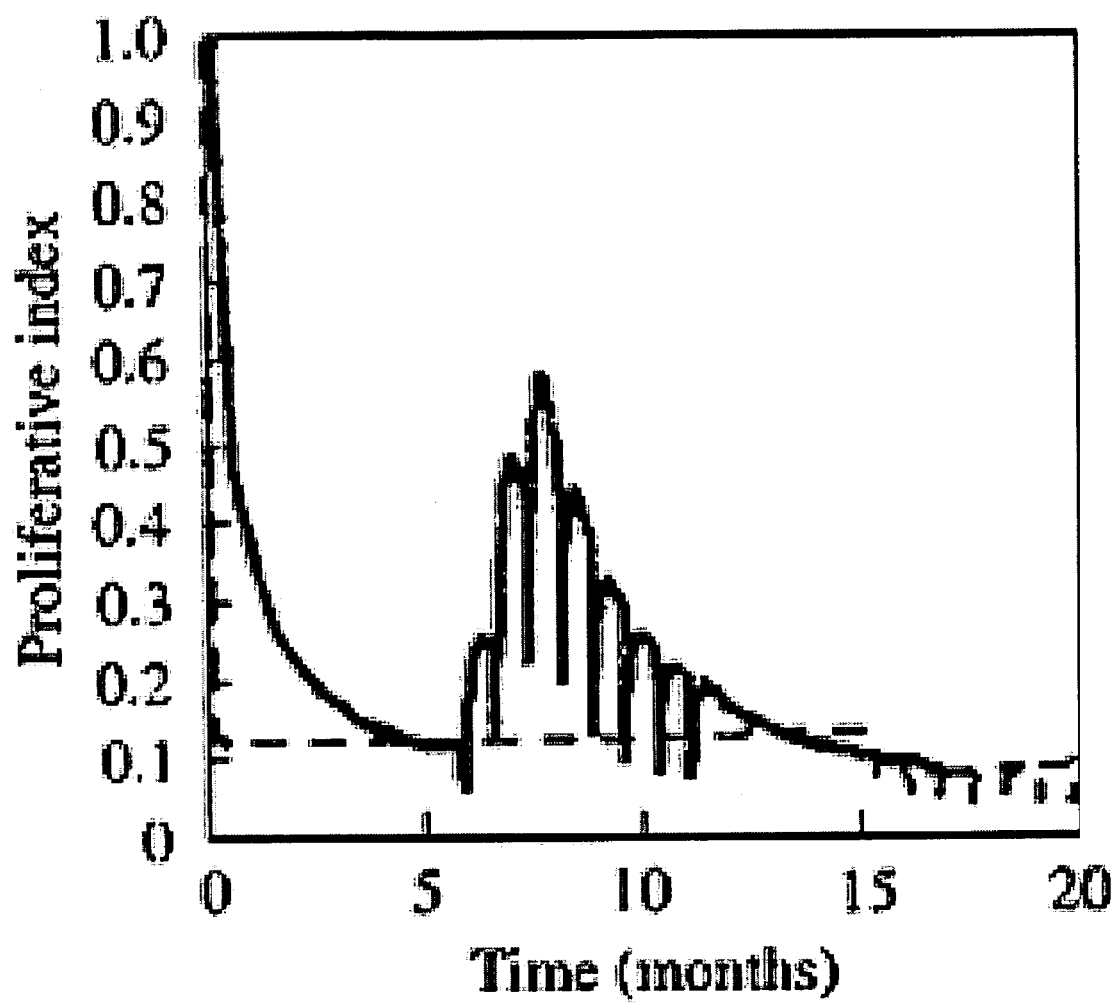
FIG. 3C is a graph of proliferative fraction vs. time under the standard schedule for the exponential and Gompertz tumors in FIGS. 3A and B. (--) Exponential; (-) Gompertzian.

A timecourse of tumor growth and evolutionary change is plotted in FIGS. 3A-D for an example using typical breast cancer kinetic parameters reported in the literature for a fairly aggressive tumor, that is, one with moderately high PI of 14%, fast c of 31-37 hr, and low AI of 0.6%. Detection is predicted to occur sooner for a tumor growing in a Gompertzian than in an exponentially growing tumor as shown in FIGS. 3A and B, assuming that they have equal values of the PI at detection. This occurs because, before detection, the Gompertzian tumor has a higher PI, so it grows more rapidly as shown in FIG. 3C. Without chemotherapy, the tumor reaches a lethal size 5-7 months after detection. With a drug regimen of CAFT given by a standard schedule of CAF every 21 days by bolus and daily oral TAM (Table 2), cure is predicted in the exponential but not the Gompertzian tumor. In the latter case, the increase in the PI when the tumor is small prevents all cells from being eliminated, resulting in death 11 months after tumor detection. The alternate schedule in which FU is given weekly by continuous infusion for 48 hr is predicted to cure both the exponential and the Gompertzian tumor. More frequent application by long infusion of this cell-cycle phase-specific drug, with its short half-life of about 15 min, achieves greater tumor toxicity, since more cells are exposed to the drug while they are in the vulnerable part of the cell cycle.

The model prediction that chemotherapy may more easily cure exponential than Gompertzian tumors is consistent with the observation that highly proliferative cancers of the blood, leukemias and lymphomas, are among the most curable. It seems likely that these tumors are more likely to follow exponential growth than large, solid tumors with poor blood perfusion. Empirical studies support the model prediction that shorter interdose intervals of CS drugs like FU are more successful than longer intervals of 3-4 weeks (Johnson et al., 1991; Toussaint et al., 1994; Hande, 1996; de Gramont et al., 1997). Some clinical studies show that interdose intervals may be reduced down to 7-14 days, compared to the 3-4 week intervals used in many protocols, without causing extreme toxicity and yet improving clinical response (Hoogstraten et al., 1976; Crown et al., 1993; Sobrero et al., 1997).

The duration of pre-clinical growth of 6-15 months, for Gompertzian and exponential growth, respectively (FIG. 3A and B), for this particular example is at the low end of the range predicted by Norton (1988) of 6 months to 9 years, and far below that predicted by Speer et al. (1984) of about 8 years. The example used here is of a fairly aggressive tumor, in which death is predicted less than a year from detection, compared to the median survival of 2.7 years for the data used in the analyses by Norton and Speer. In addition, their analyses excluded the fastest growing 77% of tumors in which the tumors were expanding too rapidly to remain undiagnosed clinically in mammograms spaced a year apart, so their predictions are biased toward slower growth. Simulations of 26 896 hypothetical tumors across a wide range of parameter values by the KITT model predict that the duration of pre-clinical growth ranges from 1.5 months to 11 years. For tumors that resulted in death between 32 and 33 months (approximately 2.7 years) after detection, the average pre-clinical growth period was 1.6 years (±3.3 months standard deviation, N=176). This is shorter than that predicted by Norton or Speer et al., but corresponds well with the empirical estimates of 1-3.8 years by Spratt et al. (1986).

FIG. 3C illustrates another model prediction that each dose of chemotherapy causes a sharp drop in the PI as a result of CS drugs killing proliferating cells and DR drugs slowing their expansion. Model runs applying only nCS drugs showed no such decline in the PI (not shown). This drop is consistent with empirical results showing a decline in Ki67 expression (an assay for PI) by more than 50% in breast cancer patients who attained a complete response to treatment (Bottini et al., 1998; Colleoni et al., 1999). In addition, different drug regimes have different affects on the proliferating fraction. Regimes with two CS drugs (MTX and FU) reduced the proliferating fraction in most tumors, while treatment with anthracyclines (nCS drugs) did not (Diadone et al., 1995).

Figure 3D:
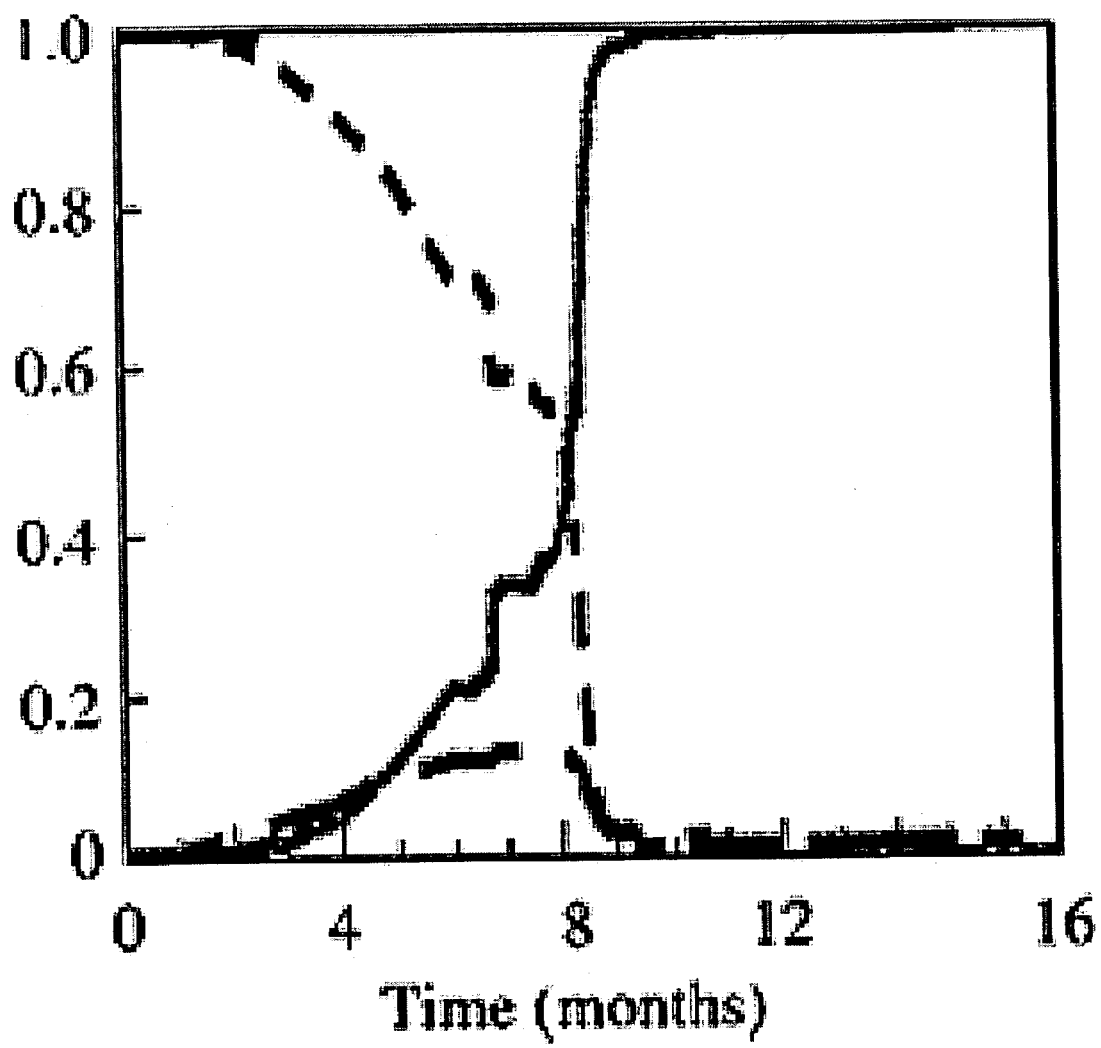
FIG. 3D is a graph of the evolution of the distribution of the cell division rate parameter b, with each line representing the fraction of cells with b=0, 1, or 2. (----) b=0; (--) b=1; (-) b=2.

FIG. 3D shows how the rate of cell division of proliferating cells is predicted to evolve in a Gompertzian tumor (shown for the alternate schedule, but similar in the standard schedule). The pattern is delayed, but essentially the same, for an exponential tumor (not shown). Initially, cells with an intermediate rate begin to replace those with a slow rate, and they, in turn, are rapidly outgrown by cells with a rapid rate of cell division. The spurts and jumps occur as a result of chemotherapy: the CS drug gives a temporary advantage to cells with a slower rate of cell division, since they enter the vulnerable part of the cell cycle less frequently, clearly visible in simulations in which only a CS drug is given (not shown). This advantage disappears as resistance to the CS drug evolves. Both nCS and cytostatic drugs, in contrast, favor cells with faster rates of cell division that re-grow more quickly between doses, also evident in simulations in which only a single drug is given (plots not shown). Cytostatic drugs, however, slow down evolutionary processes in general by reducing the number of cell generations that occur. The discordant selective pressures on the cell division rate imposed by the CS vs. the nCS and cytostatic drugs do not cancel each other out because each drug has a different half-life in the tumor tissue.

During the 6 months of chemotherapy, resistance to CS drugs is predicted to evolve faster in Gompertzian tumors than in exponential tumors [FIG. 4A]. In FIG. 4A and B, the fraction of cells with alleles conferring the highest level of resistance is plotted. Since the Gompertz tumor is detected and treated about 9 months sooner than the exponential tumor, the relevant comparison between the exponential and Gompertz curves is from the start of chemotherapy, not the time from tumor inception. The reason for faster evolution in Gompertzian tumors is that in small tumors, most cells are proliferating. Therefore, tumor growth and evolution proceed more quickly than in exponential tumors, in which only a minority of cells are proliferating whether the tumor is large or small [FIG. 3C]. Resistance to CS drugs in small Gompertz tumors evolves especially rapidly, since cells are not protected by kinetic, as opposed to genetic, resistance by virtue of being quiescent. High levels of resistance to FU only evolve for Gompertzian tumors given the alternate schedule. In the other cases (exponential or Gompertz given standard schedule), cells that are susceptible to FU make up more than 85% of the tumor even after 6 months of chemotherapy, since giving FU once every 3 weeks by bolus inflicts little cell kill, and thus only weak selection for resistance.

Resistance to CTX and ADR evolves quickly in both Gompertzian and exponential tumors experiencing either schedule of application of FU [FIG. 4B]. nCS drugs impose strong selection for resistance. Uncured tumors are predicted to be highly resistant to these two nCS drugs after 6 months of treatment.

Model results indicate that cytostatic drugs like TAM slow the evolution of resistance to cytotoxic drugs by slowing the rate of cell division. Reduced rates of cell division reduce the opportunity for resistant mutations to occur initially and subsequently limit the clonal expansion of those resistant cells. For example, applying FU alone by the alternate schedule for a Gompertzian tumor with kinetics as illustrated in FIG. 3 results in 77% of cells being highly resistant after 6 months of chemotherapy (not illustrated). If TAM is added to the regimen, however, only 17% of cells are highly resistant to FU at the end of treatment. In contrast, adding an nCS drug like ADR to the regimen of FU by the alternate schedule is predicted to facilitate the evolution of resistance to FU: 100% of the cells are highly resistant to FU after 6 months of chemotherapy with ADR and FU. This occurs because cell death caused by cytotoxics like ADR shrinks tumors, resulting in a rise in the PI, enabling fast regrowth by highly resistant cells. Thus, model results suggest that cytotoxic and cytostatic drugs differentially affect resistance evolution.

Resistance to cytostatic drugs is predicted to evolve more slowly than to cytotoxic drugs. More than 98% of cells are highly susceptible to TAM after 6 months of daily therapy with TAM alone or with TAM plus FU. As discussed above, ADR is also predicted to speed the evolution of resistance to TAM, just as to FU: after 6 months of TAM plus ADR, 82% of cells are predicted to be highly susceptible to TAM, with the remaining cells split evenly between moderate and high levels of resistance. There is no empirical data regarding the prediction about nCS drugs facilitating the evolution of resistance to cytostatic drugs. However, there is clinical data showing that resistance to DR drugs takes longer to evolve than resistance to cytotoxic therapy (Jordan & Murphy, 1990), and as a result, TAM is typically given for 5 years, compared to only 6 months for cytotoxic therapy.

The plots in FIGS. 4A and B show the marginal fractions of cells resistant to a given drug. Plots of multi-drug resistance, or the number of cells resistant to 0, 1, 2, 2, 6 drugs (summed across drugs of different identities) illustrate as to why an aggressive regimen of at least three drugs is required to cure this example tumor [FIG. 4C]. Before the tumor is even detected, there are approximately 100 cells with de novo resistance to two drugs (of any combination). Since these cells have a frequency of only $10^{-7}$, they almost certainly will not be detected in in vitro tests from tumor biopsies. Not far into treatment, cells with resistance to two-four drugs are responsible for tumor regrowth. Although in this example only four drugs were applied, the model predicts that by the end of treatment, a small fraction of cells are likely to have mutations conferring de novo resistance to other drugs to which the tumor has never been exposed, in addition to resistance to the four drugs applied.

In general, other models of the evolution of resistance to chemotherapy do not specifically incorporate each of the following factors: proliferative fraction, cell-cycle time of proliferating cells, and the natural rate of apoptosis (not caused by drugs, see references in Michelson, 1993). Instead, these models group the proliferative fraction and cell-cycle time of dividing cells into a single &&birth rate" parameter, and either assume that all cell death is caused by drugs, or group natural and drug-induced apoptosis into a single &&cell death" parameter. The tumor growth rate is calculated as their difference. Simulation results in the KITT model show that it is important not to lump parameters in this way. The model was run for two tumors, each with the same growth rate and duration of pre-clinical growth (a year), but with different rates of cell turnover. The high turnover tumor had a rapid cell-cycle time of c=25 hr, and a high PI and AI of 17 and 4%, respectively. This tumor was not predicted to be cured by a chemotherapy regimen of CAFT by the standard schedule, resulting in death about 18 months after detection. The low turnover tumor with c=55 hr, PI=11%, and AI=0.5%, in contrast, was predicted to be cured by the same regimen. The reason for this difference is that resistance evolves more quickly in the high turnover tumor, which is predicted to have 50 times more cells with high levels of de novo resistance to two drugs when treatment begins than the slow turnover tumor. In addition, acquired resistance also arises more rapidly in response to selection imposed by treatment in the high turnover tumor.

VI.J.2 Alternative Treatment Regimens

The model predicts that mono-chemotherapy does little to reduce the nadir of tumor size (i.e. the probability of cure is virtually zero), although it may prolong the time from tumor detection until patient death by 5-150%, that is, by 1-12 months, depending on the combination of cell kinetic parameters c, PI, and AI (not illustrated, range is from simulations). Adding one cytostatic drug (TAM or HER) to any single or combination regimen of cytotoxic drugs is predicted to prolong patient life by about the same amount, compared to giving the same cytotoxic regimen without the cytostatic drug. Clinical data support these predictions: statistical analyses of 75 000 women indicate greater benefits from polychemotherapy than from mono-chemotherapy, and that treatment with TAM in addition to cytotoxic chemotherapy results in longer survival than cytotoxic therapy alone (EBCTG 1992, 1998).

Treatment strategies are modified in two ways: escalating drug doses or altering the schedule of applying CS drugs. In the "High-Dose" therapy shown in FIG. 5A, standard dose intensities are increased two-fold. For the "Alternate Schedule" therapy, CS drugs are given weekly by CI for 48 hr, but the dose intensities remain the same as in the standard protocol. Schedule modifications of the nCS drugs are not shown, because the model indicates that the levels of tumor control and survival durations are virtually the same whether the nCS drugs are given according to a high concentration, infrequent pattern or a frequent, low-concentration strategy using the same total dose. Schedule modifications of the DR drugs are not illustrated because TAM is already given daily and because HER has such a long plasma half-life that more frequent HER applications do not make much difference in predicted outcomes. In addition, the model predictions using less frequent applications of TAM and HER than in the standard schedules resulted in poorer tumor control. Tumor growth parameters are the same as in the Gompertzian tumor plotted in FIG. 3.

Model results suggest that dose escalation is not as effective as altering drug schedules. Only in the six-drug regimen is high-dose therapy predicted to reduce the tumor below one cell while the standard therapy is not. In contrast, applying the CS drugs according to the alternate schedule reduces the nadir tumor size below one cell for all treatments involving CAFT (equivalent to FACT). Empirical studies supporting the model prediction that shorter interdose intervals of CS drugs are more successful than longer intervals were discussed above (Results: timecourse of tumor growth). Others have also argued that modifications in drug scheduling more effectively improve response than does dose escalation (Souhami, 1995) and that, due to the plateau of the dose response curve, reducing dose intensity below conventional dose ranges may result in lower response rates, while increases above conventional doses may not improve outcomes. Clinical trial data support this argument: some studies (Hortobagyi et al., 1987; Wood et al., 1994) found that high-dose combination chemotherapy for breast cancer using CAF did not significantly improve outcomes and was significantly more toxic than the standard dose CAF regimen.

VI.J.3 Contrasting Tumor Kinetics and Treatment Regimens

To illustrate how cell kinetics may differentially affect treatment outcome, two Gompertzian tumors with contrasting cell kinetics are compared: a &&low-PI tumor" with PI=5%, AI=0.5%, and c=50 hr, and a &&high-PI tumor" with PI=50%, AI=3.5%, and c=30 hr. Because AI's are correlated with PI's (Höckel et al., 1999; Lipponen, 1999; Matsushima et al., 1999), the apoptotic rates modeled were chosen to be greater in highly proliferative tumors and to parallel rates in the literature. A plot of the nadir tumor size achieved by different drug combinations for these two tumors illustrates these predictions [FIG. 5B]. First, regimens with two nCS drugs (ADR and CTX, or A and C, respectively) are more effective (achieve lower nadirs) in patients with a low PI than with a high PI, while regimens with two CS drugs (FU and MTX, or F and M) are more effective in patients with a high than with a low PI. Second, FAC (or CAF) chemotherapy is predicted to be more effective than CMF chemotherapy for both low- and high-PI tumors. The magnitude of the superiority of FAC over CMF is greater in low-PI tumors. Third, cytostatic drugs (TAM and HER, or T and H) are predicted to be an important part of many regimens, as they may make the difference between a non-curative and a curative combination of cytotoxics. For example, FAC is predicted to cure neither the low nor the high-PI tumor, FACH is predicted to cure only the low-PI tumor, and FACTH is predicted to cure both. Cytostatic drugs are important because they slow tumor regrowth between doses of cytotoxic drugs and because they slow the evolution of drug resistance, as discussed above.

The first model prediction is borne out in empirical studies showing that patients whose tumors have a high PI or SPF respond better to chemotherapy with CS drugs but have shorter relapse-free survival (Gamel et al., 1995; Mac-Grogan et al., 1996; Silvestrini et al., 1997; Collecchi et al., 1998; Stapleton et al., 1998; Sinicrope et al., 1999). In one study of oral cavity cancers, survival of patients with rapidly proliferating tumors was about three-fold higher with a triple drug combination of vincristine, bleomycin, and methotrexate (which are all CS drugs) than with only vincristine and bleomycin (Molinari et al., 1991). Conversely, with slowly proliferating tumors, patients given the two-drug combination of vincristine and bleomycin did better than those given methotrexate as well as the other two CS drugs. In a study of ovarian cancer, Silvestrini et al. (1992) found that patients with slowly proliferating tumors had longer survival after treatment with an nCS drug than did patients with rapidly proliferating tumors.

The second model prediction described above, that FAC more effectively reduces tumor size and prolongs patient life than CMF, is also supported by clinical findings. Investigators report that approximately 50% of patients with advanced breast cancer have an objective response to CMF, compared to 75% of patients showing an objective response to FAC (Hortobagyi et al., 1987; Andersson et al., 1999).

In support of the third model prediction, the Early Breast Cancer Trialists' Group (EBCTG) found that using the cytostatic agent TAM in conjunction with cytotoxic polychemotherapy was better than using cytotoxic drugs alone or TAM alone (1992, 1998). The inclusion of the cytostatic drug HER in treatment regimens for women with HER2 overexpression also results in significantly higher response rates and longer times to progression than cytotoxic chemotherapy alone (Pegram et al., 1998). Other clinical results also support model predictions that CS, nCS, and DR drugs are best used in combination because they may act synergistically (reviewed by Jordan & Murphy, 1990).

VI.J.4 Test of the Model Using Published Data

Simulations to model the study by Silvestrini et al. (2000) and Bonadonna et al. (1995) show that for tumors with a reasonable potential for cure (with a nadir of 10 or fewer cells), the sequential treatment results in a significantly smaller nadir size (and thus a higher chance of cure) than does the alternating schedule [FIG. 6A, p(0.009, Student's t-test, df=16]. For patients in which the chance of cure is negligible, however, the duration of survival was the same under both schedules [FIG. 6B, p=0.99, df=224]. Tumors with a decent chance of cure had a significantly lower PI of approximately 6% than incurable tumors of 10% (p(0.002, df=242). These model results concur with the clinical findings that the sequential regimen resulted in higher survival rates than the alternating schedule for tumors with a low rate of proliferation (with a TLI of 5% or less). Also, simulations are consistent with the empirical result that the schedules were equivalent for patients in which the TLI was high, and that the prognosis was worse for patients whose tumors had a high rate of proliferation than for those with a low rate of proliferation.

VI.J.5 Prognostic Trees

Decision trees constructed from the simulation of 26 896 tumors indicate that the variables v and p (rate of necrosis and transition rate from the quiescent to the proliferating compartment) did not have significant enough effects to determine the nodes to any branches in either of the trees for the probability of survival or for the duration of survival. A wide range of values were simulated since empirical estimates of these two parameters are difficult to obtain. This result indicates that it is sufficient to measure only the variables AI, PI, and c, and to know which drugs are used and their doses and schedules, as these factors all determined the nodes of the prognostic trees (FIG. 7). The numbers associated with each drug represent dose intensities (normalized, as discussed in Appendix C). The deepest branches of the tree for the probability of survival [FIG. 7A] show that applying too low a dose of CTX and/or ADR is likely to result in patient death, regardless of tumor kinetics. The other drugs, HER, FU, MTX and TAM interact with tumor kinetic factors, which determine the nodes closer to branch tips. For example, following the far-right branch in FIG. 7A shows that if a patient receives the combination CAH, and also a sufficient dose of eitherMTX or FU, she is likely to live. If MTX or FU are not given or are given at too low a dose, a patient with a PI less than 27% still might be likely to live. However, if a patient's PI is above 28%, then a high likelihood of survival depends on the cell-cycle time being longer than 45 hr. Survival durations are predicted to be longer for patients who receive chemotherapy and whose tumors have a long cell-cycle time, high AI, and low PI, factors which result in slow tumor growth [FIG. 7B].

VI.J.6 Toxicity

Bone marrow stem cells are predicted to suffer slightly higher mortality if they spend 14 days, rather than 4 days, in the quiescent state because they do not recover as quickly between doses the pattern of toxicity in response to different drug combinations and schedules, however, is similar for the 4- and 14-day quiescence durations, so only that for the 4-day quiescence is illustrated (FIG. 7). Using the same dose response and drug concentration parameters as in the completely susceptible tumor results in model predictions of extreme toxicity to the bone marrow, even for standard treatments like FACT chemotherapy, which have been shown to be effective and not excessively toxic in the clinic. Thus, the drug concentration parameters for &&standard dose" therapy in the bone marrow were modified to be one-third of those found in the tumor. This is equivalent either to saying that the concentration is lower in the bone marrow than the tumor, or that the concentration is the same but the scaling parameter a in the dose response curve is only a third of the value in the tumor for each drug. This higher toxicity in the bone marrow than in the tumor for equivalent doses occurs because drug resistance does not evolve in the bone marrow. High-dose chemotherapy (doses double those in the standard regimen to the bone marrow) involving ADR and CTX are predicted to be more toxic than those not involving an nCS drug. A number of runs of the model varying the dose and schedule of FU and MIX indicate that toxicity is affected by their schedule but that dose has very little effect (not plotted). Modeling bone marrow toxicity predicts that regimens including CAF are most toxic, especially if FU is given weekly by 48 hr of CI rather than every 21 days by bolus. If the CS drugs are given weekly by bolus rather than by CI, however, CAF is not predicted to be overly toxic (not shown); nor is CAF predicted to be overly toxic if FU is given every 3 weeks by CI for 48 hr, so it is only when FU is given both weekly and by 48 hr of CI that CAF is predicted to be highly toxic.

Clinically, myelosuppression has been found to be related more to the duration of CI than to the dose of CS drugs (Price, 1987), supporting the model prediction that the alternative schedule may be more toxic than the standard schedule. However, if toxicity is related to peak drug concentration then frequent infusions may be less toxic than infrequent bolus applications, as has also been observed in clinical trial results (Shah et al., 1985; Hande, 1996). Mathematical calculations indicate that if drugs are given by bolus every 3 weeks, then peak concentrations are 298, 13, 25, and 5 times higher for FU, MTX, CTX, and ADR, respectively, than if the same dose intensity is given by weekly infusions for 48 hr. Thus, if toxicity is a function of peak concentration, infrequent bolus administration may be substantially more toxic than frequent infusions.

Alternatively, toxicity may be a function of the relative average dose intensity. Using all six drugs at the standard doses, this intensity is one. The relative average dose intensity for combinations using 5, 4, or 3 drugs is 5/6, 2/3, or 1/2, respectively. The relative average dose intensity for high-dose therapy with two-fold higher dose intensity using all six drugs is 2. Thus, if toxicity were a direct multiple of the average relative dose intensity, then single-drug regimens at the standard dose intensities would inflict only one-sixth the toxicity of the six-drug regimen. Finally, toxicity may instead be a function of the cumulative amount of drug given. Clinically, this is known to be true for the cardiotoxicity of ADR.

VI.K. Discussion and Conclusions

A KITT model of multi-drug cancer chemotherapy was developed to elucidate as to how treatment may be tailored for individuals based on tumor cell kinetic parameters that can be easily measured from tumor biopsies. The model generates a number of predictions that are consistent with results of clinical studies published in the literature. For example, altering drug scheduling may be more effective than dose escalation; more frequent application of CS drugs by CI may be more effective than infrequent application by bolus at the same dose intensity. Theoretical results suggest that cytostatic drugs should be applied in conjunction with cytotoxic drugs to slow tumor regrowth between applications and to delay the evolution of drug resistance. Tumor kinetics are predicted to affect the response to drugs, such that tumors with a high PI may respond better to CS drugs than tumors with a low PI, while tumors with a low PI are predicted to respond better to nCS drugs. Finally, results indicate that CAF therapy is more effective than CMF therapy. Relevant empirical studies were discussed.

As discussed above, the computational approach of the present invention, which differentiates drugs based solely on their half-lives, cell-cycle phase specificities, and schedule of application, generates results matching those observed empirically. Modeling some possible drug combinations, however, may require that KITT be modified to incorporate more biochemical detail. Synergism or negative interactions among drugs may depend on specific biochemical reactions and may require Michaelis-Menten kinetics or other descriptions of protein binding to be combined with the simple dose response models used here. In addition, more complex cell cycle arrests in a particular phase or abrogation of arrest may be important. Models with such drug interactions are currently being developed by the author based on data from extensive cell culture studies. While more detailed models may be helpful in particular cases, their drawback is that much more data from a given individual's tumor would need to be gathered, which could become too impractical and expensive for the clinic.

With some parameter modifications to the model of the tumor cell population, the same kinetic model of cell growth and drug response was used to model the bone marrow stem cell population. These calculations suggest that drug regimens including CAF may be relatively toxic to the bone marrow, particularly if high doses of ADR and CTX are applied or if FU is given weekly by CI for 2 days rather than by bolus or once every 3 weeks. However, limiting toxicity depends on the drug and the tissue involved, and must be explored on an individual basis depending on the patient's health status and prognosis (Is chemotherapy for cure or for palliation of pain?). Alternative measures of toxicity such as cumulative dose, average relative dose intensity, and peak drug concentration yield different predictions about which regimens are likely to be the most toxic.

The KITT computational model of multidrug chemotherapy designed to predictively tailor treatments for individuals in terms of the drug combination administered and at what doses and schedules[1]. It individualizes treatments based on cell kinetic parameters from tumor biopsies. Evolution of drug resistance, perhaps the primary reason for treatment failure, is a key component of KITT. In addition, the model incorporates the genetic and kinetic heterogeneity of a tumor undergoing treatment with combinations of cytostatic and cytotoxic cell-cycle phase-specific and phase-nonspecific drugs.

The software incorporates a number of realistic sub-models to capture the dynamics of drug pharmacokinetics and pharmacodynamics and evolution within the tumor. The required patient-specific model inputs are proliferative index, apoptotic index, S-phase fraction, cell cycle time, and level of drug resistance, all of which are routinely requested by clinical oncologists. Given values for those same cell cycle parameters from toxicity-limiting stem cell populations such as bone marrow or GI tract, the model may also be useful to predict toxicity of some competing regimens.

In clinical research, this software may streamline the design of clinical trials by predicting those drug combinations, doses, and schedules most likely to improve outcomes in specific groups of patients. Thus, KITT is a tool that has the potential to guide the design of rational drug combinations and schedules.

In addition, KITT may help to identify a kinetically homogeneous group of patients, in terms of predicted response, for which a given regimen may be most beneficial. Thus, this software may guide patient selection and division into subgroups, increasing the statistical power of clinical trials.

Cell kinetics provide predictive as well as prognostic information[2-5], so it is logical to use this information in selecting treatments. Mathematical investigation of the complex interactions among the proliferative fraction, apoptosis, S-phase fraction, drug combination, and drug resistance evolution is long overdue. Individually, each of these features has been clinically investigated and shown to correlate with patient outcome[2,5-8]. Now KITT takes the novel, comprehensive approach to tie all of these variables together in a mechanistic model. Furthermore, KITT requires as input only those parameters that can be reasonably estimated from tumor biopsies, rather than a complicated suite of transition rate probabilities with no obvious link to clinical assay results and which are infeasible if not impossible to measure from tumor biopsies, which are required by other computational models of cancer chemotherapy.

KITT may aid physicians and scientists in predicting not only how a given patient's tumor will likely grow in response to alternative treatments, but also how rapidly resistance may evolve to a particular drug, and potential ramifications of treatment modification in that patient. This may be a useful tool in helping a patient and physician decide whether a more toxic treatment is "worth it" in prolonging life or increasing the chance of cure.

KITT enables an exploration of hypotheses that would be impossible in a clinical setting. In some cases it suggests tradeoffs (e.g. drug scheduling, rate of resistance evolution to different drugs in combination) that one would not expect without detailed quantitative and mechanistic analyses. Thus, this mechanistic model promises to facilitate our understanding of in vitro, in vivo, and clinical trial results. Moreover, as empirical data suggest aspects of the model that need elaboration or modification, these can be incorporated.

In conclusion, KITT is a tool that may help guide the selection of rational drug combinations in early stage clinical trials, classify patients into kinetically homogeneous subgroups most likely to respond to given regimens, and provide individual, tailored prognostic and predictive information.

VI.L. APPENDIX A: Equations for the Rate of Change of Each Subpopulation of Tumor Cells Table 1 presents definitions of all parameters, variables, and functions used in the model. The number of cells within a tumor at time t with the specified alleles at the resistance and kinetic loci is $N_x(r_{CS1}, r_{CS2}, r_{nCS1}, r_{nCS2}, r_{DR1}, r_{DR2}, b, d, t)$, where x=P for proliferating and x=Q for quiescent cells. This quantity will be represented as $N_x(t)$ when the allelic indices can be inferred. The proliferating fraction of cells is $N_P(t)/[N_P(t)+N_Q(t)]$ and may be estimated empirically, for example, by staining with the Ki67 antibody or by flow cytometry. The size of each subpopulation $N_x(r_{CS1}, r_{CS2}, r_{nCS1}, r_{nC2}, r_{DR1}, r_{DR2}, b, d, t)$ increases from cells that divide, survive division, and do not mutate, as well from cells in other genetic subpopulations that divide, survive division, and do mutate. When a cell divides, mutations may occur at any of the 8 loci. The chance of two mutations occurring in a single cell in one cell division is negligible compared to the probability of two mutations occurring in two different cell divisions so it is assumed to be zero. In addition, drug-inflicted cell death diminishes the size of each subpopulation. Finally, natural apoptosis reduces the number of cycling cells, and necrosis diminishes the size of the quiescent subpopulation.

Ignoring mutations, the rate of change of the number of proliferating tumor cells is $$\frac{dN_P(t)}{dt} = (B - k - q)N_P(t) + pN_Q(t), \quad (A1)$$

as the size of the subpopulation increases from cell division, decreases from drug-induced kill and natural apoptosis at a rate k, and also declines as cells enter the quiescent state at a rate q. Quiescent cells enter the proliferating compartment at a rate p. The quiescent fraction of cells changes according to $$\frac{dN_Q(t)}{dt} = qN_P(t) - \left[p + 1 - \prod_j s_{nCS}(j) + v\right]N_Q(t), \quad (A2)$$

as proliferating cells enter the quiescent state at a rate q, quiescent cells return to the cycling compartment at the rate p, and cells die as a result of the nCS drug or necrosis at rates of $$\left(1 - \prod_j s_{nCS}(j)\right)$$

and v, respectively, where $s_{nCS}(j)$ is the probability per unit time of surviving the $j^{th}$ nCS drug. The dynamics of the quiescent subpopulations are not altered by mutation. If no drugs are applied, then Equations A1-A2 form a system of linear differential equations that can be solved analytically. An Excel spreadsheet is available from the author (gardner26@llnl.gov) for plotting tumor growth versus time, the growth fraction, and the necrotic fraction. The user specifies values of the cell cycle time (c) the PI, the AI, and the transition rates from the quiescent compartment to the proliferating compartment and necrosis (expressed as the mean residence time in the quiescent state before reentering the proliferating compartment (1/p), and the mean residence time in the quiescent state before necrosis, 1/v). The transition rate from the resting to the proliferating compartment and the rate of necrosis are difficult to measure, so the Excel spreadsheet enables one to estimate outer bounds on these parameters. Simulations described here (see Results) indicate that these two parameters are not very important for prognoses of the probability of cure and survival duration, as they do not appear as significant factors in decision tree algorithms examining these prognostic variables.

The model above conceptually follows that of Norton and Simon (1977) in that, for CS drugs, the number of cells killed by cycle specific agents depends on the growth fraction and the tumor size. The general form of these equations is similar to that used before (Panetta 1997) in modeling treatment with Taxol. The model here differs from that by Panetta, however, because this model includes evolutionary change within the tumor, Gompertzian growth, and treatment using multiple drugs with contrasting effects on cell kinetics. It also allows one to specify not only whether quiescent or only proliferating cells are affected by a given drug, but also whether a drug affects only a fraction of cells which are proliferating (e.g. those in M-phase). Finally, this model more realistically incorporates dose response and drug pharmacokinetics.

Including mutation in Equation A1 requires modification of the equation for the rate of change of the number of proliferating cells, which becomes $$\frac{dN_p(t)}{dt} = -N_p(t)[k + D_a + q] + \quad (A3)$$
$$[1-\mu_{RL}]^6[1-\mu_{KL}]^6 M_{small} +$$
$$\mu_{RL}[1-\mu_{RL}]^5[1-\mu_{KL}]^2 M_R +$$
$$[1-\mu_{RL}]^6[1-\mu_{KL}]\mu_{KL} M_K,$$

where $M_{small}$ is the increase in a subpopulation from cell division in which no mutations occur or a mutation of small effect occurs at either a resistance or a kinetic locus, given by $$M_{small} = \sum_{i_1=0}^{1}\sum_{j_1=0}^{1}\sum_{k_1=0}^{1}\sum_{i_2=0}^{1}\sum_{j_2=0}^{1}\sum_{k_2=0}^{1}\sum_{l=-1}^{1}\sum_{m=-1}^{1} \quad (A4)$$
$$\{N_p(r_{CS1}-i_1, r_{CS2}-i_2, r_{CNS1}-j_1, r_{CNS2}-j_2,$$
$$r_{DR1}-k_1, r_{DR2}-k_2, b-l, d-m, t) \times$$
$$B(b-l, Z_{DR1}(r_{DR1}-k_1, y_{DR1}(t)),$$
$$Z_{DR2}(r_{DR2}-k_2, y_{DR2}(t))) \times$$
$$\mu_{RS}^{|i_1|+|i_2|+|j_1|+|j_2|+|k_1|+|k_2|}$$
$$[1-\mu_{RS}]^{6-(|i_1|+|i_2|+|j_1|+|j_2|+|k_1|+|k_2|)}$$
$$\mu_{KS}^{|l|+|m|}[1-\mu_{KS}]^{2-|l|-|m|}\}.$$

As discussed above, whenever $M_{small}$ is computed, terms with multiple mutations that are multiplied by factors of $\leq 10^{-8}$ are ignored. This simplification speeds the program substantially and makes virtually no difference in the results. $M_R$ represents the change in the size of a fully resistant subpopulation given that a large resistance mutation has occurred:

$$M_R = \sum_{i=0}^{r_{max}} H_{CS1}BN_p(i, r_{CS2}, r_{nCS1}, r_{nCS2}, r_{DR1}, r_{DR2}, b, d, t) + \quad (A5)$$
$$\sum_{i=0}^{r_{max}} H_{CS2}BN_p(r_{CS1}, i, r_{nCS1}, r_{DR1}, r_{DR2}, b, d, t) +$$
$$\sum_{i=0}^{r_{max}} H_{nCS1}BN_p(r_{CS1}, r_{CS2}, i, r_{nCS2}, r_{DR1}, r_{DR2}, b, d, t) +$$
$$\sum_{i=0}^{r_{max}} H_{nCS2}BN_p(r_{CS1}, r_{CS2}, r_{nCS1}, i, r_{DR1}, r_{DR2}, b, d, t) +$$
$$\sum_{i=0}^{r_{max}} H_{DR1}N_p(r_{CS1}, r_{CS2}, r_{nCS1}, r_{nCS2}, i, r_{DR2}, b, d, t)$$

-continued
$$B(b, Z_{DR1}(i, y_{DR1}(t)), Z_{DR2}) +$$
$$\sum_{i=0}^{r_{max}} H_{DR2}N_p(r_{CS1}, r_{CS2}, r_{nCS1}, r_{nCS2}, r_{DR1}, i, b, d, t)$$
$$B(b, Z_{DR1}, Z_{DR2}(i, y_{DR2}(t))).$$

where $H_j=1$ if $r_j=r_{max}$ and $H_j=0$ otherwise. Similarly, $M_K$ is the change in the size of a subpopulation with the maximum or minimum values of b or d, given that a large kinetic mutation has occurred:

$$M_k = \sum_{i=0}^{b_{max}} H_b N_p(r_{CS1}, r_{CS2}, r_{nCS1}, r_{nCS2}, r_{DR1}, r_{DR2}, i, d, t) \quad (A6)$$
$$B(i, Z_{DR1}, Z_{DR2}) +$$
$$\sum_{i=0}^{d_{max}} H_d BN_p(r_{CS1}, r_{CS2}, r_{nCS1}, r_{nCS2}, r_{DR1}, r_{DR2}, b, i, t).$$

where $H_b=1$ if $b=0$ or $b_{max}$ and $H_b=0$ otherwise, and $H_d=1$ if $d=0$ or $d_{max}$ and $H_d=0$ otherwise. $N_x(t)$ was calculated by numerical integration with the 5th order Cash-Karp Runge-Kutta method with adaptive stepsize control, using algorithms modified from Press et al. (Press et al. 1992).

To model resection, the size of each tumor subpopulation $N_x(t^*)$ is noted at the time $t^*$ when the tumor first grows to 99% of the size when it will be detected at time $t_{SEE}$. The number of cells in this tissue will be surgically removed. Upon detection, each tumor subpopulation is reduced to $N_x(t_{SEE})-N_x(t^*)$, the number of cells missed in surgery, and then chemotherapy begins.

VI.M. APPENDIX B: Calculating q

This linear system of differential equations given by Eq. A1-A2 with $$\left(1-\prod_j s_{nCS}(j)\right) = 0$$

before any drugs are applied can be solved with the initial conditions $N_p(0)=1$ and $N_q(0)=0$. The PI can be measured empirically, and is given by $$PI = \frac{N_p(t_{see})}{N_p(t_{see}) + N_q(t_{see})}.$$

Then, one can solve for q at tumor detection in terms of the empirically determined rate of cell division B in proliferating cells, apoptosis A, and the assumed values of p and v, giving $$q = \frac{2(p+v+B-A)2PI/(1-PI)+4p}{(2PI/(1-PI)+1)^2-1}. \quad (B1)$$

VI.N. APPENDIX C: Drug Effects

The drug concentration of the ith DR drug is $y_{DRi}(t)$. DR drugs slow the progress of cells through the cell cycle. The dose response curve for the delay of progression through the cell cycle is given by $$Z_{DRi}(r_i, y_{DRi}(t), a_i) = z_{max}[1 - e^{-a_i(r_{max} - r_i)y_{DRi}(t)}] \quad (C1)$$

which saturates at $z_{max}$ hours at high drug concentrations (here assumed to be 24 hours) and approaches this maximum delay at a rate that depends on resistance $r_i$ and the factor $a_i$ which scales drug concentration depending on the units of measurement. To simplify presentation of the model, we will sometimes refer to $Z_{DRi}(r_i, y_{DRi}(t), a_i)$ as $Z_{DRi}$.

The probability per unit time that a cell with resistance $r_i$ survives the $i^{th}$ CS drug is modeled using the Exponential Kill (EK) model (Gardner 2000a):

$$s_{CS}(r_i, B, f_i, y_i, a_i) = 1 - (f_i - \tau_i B + B)(1 - e^{-a_j(r_{max} - r_j)y_i(t)}) \quad (C2).$$

where $f_i$ is the fraction of cells in the vulnerable part of the cell cycle at the beginning of drug exposure at time t=0, and $\tau$=minimum($f_i$c,t). Similarly, the probability per unit time of surviving the $j^{th}$ nCS drug is $$s_{nCS}(r_j, y_j, a_j) = e^{-a_j(r_{max} - r_j)y_i(t)} \quad (C3).$$

Drug doses for a standard regimen were normalized so that the scaling factor $a_i$ in Equations C1-C3 for each drug equals one. This was done by generating dose response curves of the nadir of tumor size in response to six months of chemotherapy (with only that one drug) at the standard schedule in Table 2 versus the dose intensity used, assuming a value of $a_i$=1. The nadir plateaus at high dose intensities, and the minimum dose intensity for which survival is near the plateau (<15% from the asymptote) was found numerically.

Assuming that there is no cross-resistance and that the probabilities of surviving each drug are independent of one another and of the probability that a cell dies by natural apoptosis, the probability of death of a cell in the proliferating compartment per unit time is $$k = 1 - (1 - D_a) \prod_i s_{CSi}(r_i, B, f_i, y_i, a_i) \prod_j s_{nCS}(r_j, y_j, a_j). \quad (C4)$$

VI.O. APPENDIX D: Drug Concentration

In the results presented here, a single-compartment model of drug concentration is used, although more complicated, multi-compartmental models are recommended in future modifications. An average dose intensity (amount of drug delivered per unit time) of $\bar{y}_i$ mg/m² hour⁻¹ is given. Holding dose intensity constant, treatments are given at intervals of u hours of magnitude $u\bar{y}_i$ mg/m². The drug is infused for a duration of h hours at a rate of $u\bar{y}_i/h$ mg/m² hour⁻¹, and the concentration declines exponentially at a rate $\lambda$ characterised by the drug's half life of $\log_e(2)/\lambda$ hours (=0.693/$\lambda$ hours). If drug application starts at t=0 and y(0)=0, the drug concentration at time t is $$y(t) = \begin{cases} \dfrac{u\bar{y}/h}{\lambda}(1 - e^{-\lambda t}) + x & \text{for } t \leq h \\ \dfrac{u\bar{y}/h}{\lambda} e^{-\lambda t}(e^{\lambda h} - 1) + x & \text{for } t > h \end{cases} \quad (D.1)$$

where $$x = \sum_{i=1}^{PA} \frac{u\bar{y}/h}{\lambda} e^{-\lambda(u_i + t_{AD})}(e^{\lambda h} - 1) \quad (D.2)$$

is the amount of drug built up from previous drug applications that has not yet been fully excreted or metabolized. $t_{AD}$ is the time after the start of infusion of the last dose, calculated as $t_{AD}$=t mod u (the remainder of dividing t by u) and PA is the number of previous drug applications, calculated as the integer part of t/q. The dose intensity, frequency of application and duration of infusion of each drug may differ from that of other drugs.

VI.P. References

1. ACAR, J. F. & GOLDSTEIN, F. W. (1998). Consequences of increasing resistance to antimicrobial agents. *Clin. Infect. Dis.* 27, S125-S130.

2. ALITALO, K. (1985). Amplification of cellular oncogenes in cancer cells. *TIBS*, 10, 194-197.

3. ANDERSSON, M., MADSEN, E. L., OVERGAARD, M., ROSE, C., OMBERNOWSKY, P. & MOURIDSEN, H. T. (1999). Doxorubicin versus methotrexate both combined with cyclophosphamide, 5-fluorouracil and tamoxifen in postmenopausal patients with advanced breast cancer*a randomized study with more than 10 years follow-up from the Danish Breast Cancer Cooperative Group. *Eur. J. Cancer* 35, 39-46.

4. BAKER, F. L., SANGER, L. J., RODGERS, R. W., JABBOURY, K. & MANGINI, O. R. (1995). Cell proliferation kinetics of normal and tumor tissue in vitro: quiescent reproductive cells and the cycling reproductive fraction. *Cell Prolif.* 28, 1-15.

5. BARRANCO, S. C., TOWNSEND, C. M., JENKINS, V. K., KOESTER, S. K., HO, B. Y. & REUMONT, K. J. (1988). Treatment-induced changes in sensitivity in a multiclonal human tumor mixture model in vitro. *Cancer Res.* 48, 2749-2755.

6. BEGG, A. C. (1997). Cell proliferation in tumors. In: *Basic Clinical Radiobiology*. (Steel, G. G., ed.), pp. 14-22. New York: Oxford University Press, Inc.

7. BIRKHEAD, B. G., RANKIN, E. M., GALLIVAN, S., DONES, L. & RUBENS, R. D. (1987). A mathematical model of the development of drug resistance to cancer chemotherapy. *Eur. J. Cancer Clin. Oncol.* 23, 1421-1427.

8. BONADONNA, G., ZAMBETTI, M. & VALAGUSSA, P. (1995). Sequential or alternating doxorubicin and CMF regimens in breast cancer with more than three positive nodes. *JAMA* 273, 542-547.

9. BOTTINI, A., BERRUTI, A., BERSIGA, A., BRUNELLI, A., BRIZZI, M. P., DI MARCO, B., CIRILLO, F., TAMPELLINI, M., BOLSI, G., AGUGGINI, S., BETRI, E., FILIPPINI, L., BERTOLI, A., ALQUATI, P. & DOGLIOTTI, L. (1998). Cytotoxic and antiproliferative activity of the CMF regimen administered in association with tamoxifen as primary chemotherapy in breast cancer patients. *Int. J. Oncol.* 13, 385-390.

10. BYRNE, H. M. & CHAPLAIN, M. A. J. (1996). Growth of necrotic tumors in the presence and absence of inhibitors. *Math. Biosci.* 135, 187-216.

11. CALLERA, F. & FALCAO, R. P. (1997). Increased apoptotic cells in bone marrow biopsies from patients with aplastic anaemia. *Br. J. Haematol.* 98, 18-20.

12. CAREY, J. R. (1982). Demography and population dynamics of the Mediterranean fruit fly. *Ecol. Model.* 16, 125-150.

13. CHABNER, B. A. (1993). Anticancer drugs. In: *Cancer* (DeVita, J. V. T., Hellman, S. & Rosenberg, S. A., eds), pp. 325-340. Philadelphia: Lippincott.

14. COLDMAN, A. J. & GOLDIE, J. H. (1987). Impact of doseintense chemotherapy on the development of permanent drug resistance. *Semin. Oncol.* 14, 29-33.

15. COLLECCHI, P., GALDINI, E., GIANNESSI, P., NACCARATO, A. G., PASSONI, A., GARDIN, G., RONCELLA, M., EVANGELISTA, G., BEVILACQUA, G. & CONTE, P. F. (1998). Primary chemotherapy in locally advanced breast cancer (LABC): e!ects on tumour proliferative activity, bcl-2 expression and the relationship between tumour regression and biological markers. *Eur. J. Cancer* 34, 1701-1704.

16. COLLEONI, M., ORVIETO, E., NOLE, F., ORLANDO, L., MINCHELLA, I., VIALE, G., PERUZZOTTI, G., ROBERTSON, C., NOBERASCO, C., GALIMBERTI, V., SACCHINI, V., VERONESI, P., ZURRIDA, S., ORECCHIA, P. & GOLDHIRSCH, A. (1999). Prediction of response to primary chemotherapy for operable breast cancer. *Eur. J. Cancer* 35, 574-579.

17. CROWN, J., KRITZ, A., VAHDAT, L., REICH, L., MOORE, M., HAMILTON, N., SCHNEIDER, J., HARRISON, M., GILEWSKI, T., HUDIS, C., GULATI, S. & NORTON, L. (1993). Rapid administration of multiple cycles of high-dose myelosupressive chemotherapy in patients with metastic breast cancer. *J. Clin. Oncol.* 11, 1144-1149.

18. DANOVA, M., MAZZINI, G., ALBERICI, R., LUCOTTI, C., PALMERI, S., FINCATO, G., CAZZOLA, M., RICCARDI, A. & ASCARI, E. (1996). Sequential administration of interleukin-3 and granulocyte-macrophage colony-stimulating factor following intensified accelerated CEE (cyclophosphamide, epirubicin, etoposide) chemotherapy in patients with solid tumors: cytokinetic elects on bone marrow hematopoietic progenitors. *Int. J. Oncol.* 9, 971-976.

19. DAY, R. S. (1986). Treatment sequencing, asymmetry, and uncertainty: protocol strategies for combination chemotherapy. *Cancer Res.* 46, 3876-3885.

20. DAY, R. S. (2000). OncoTCap. http://www.oncotcap.pci.upmc.edu/tcap/2000/, University of Pittsburgh (PITT).

21. DE GRAMONT, A., BOSSET, J. F., MILAN, C., ROUGIER, P., BOUCHE, O., ETIENNE, P. L., MORVAN, F., LOUVET, C., GUILLOT, T., FRANCOIS, E. & BEDENNE, L. (1997). Randomized trial comparing monthly low-dose leucovorin and fluorouracil bolus with bimonthly high-dose leucovorin and fluorouracil bolus plus continuous infusion for advanced colorectal cancer: a French intergroup study. *J. Clin. Oncol.* 15, 808-815.

22. DIADONE, M. G., SILVESTRINI, R., LUISI, A., MASTORE, M., BENINI, E., VENERONI, S., BRAMBILLA, C., FERRARI, L., GRECO, M., ADREOLA, S. & VERONESI, U. (1995). Changes in biological markers after primary chemotherapy for breast cancers. *Int. J. Cancer* 61, 301-305.

23. Early Breast Cancer Trialists' Group (1992). Systemic treatment of early breast cancer by hormonal, cytotoxic, or immune therapy. *,ancet* 339, 1-15, 71-85.

24. Early Breast Cancer Trialists' Group (1998). Polychemotherapy for early breast cancer: an overview of the randomised trials. *,ancet* 352, 930-942.

25. GAMEL, J. W., MEYER, J. S. & PROVINCE, M. A. (1995). Proliferative rate by S-phase measurement may a!ect cure of breast carcinoma. *Cancer* 76, 1009-1018.

26. GARDNER, S. N. (2000a). A mechanistic, predictive model of dose response curves for cell cycle phase-specific and -nonspecific drugs. *Cancer Res.* 60, 1417-1425.

27. GARDNER, S. N. (2000b). Scheduling chemotherapy: catch 22 between cell kill and resistance evolution. *J. $^1$heor. Med.* 2, 1-18.

28. GARDNER, S. N., GRESSEL, J. & MANGEL, M. (1998). A revolving dose strategy to delay the evolution of both quantitative vs. major monogene resistances to pesticides and drugs. *Int. J. Pest Manag.* 44, 161-180.

29. GASPARINI, G., POZZA, F., MELI, S., REITANO, M., SANTINI, G. & BEVILACQUA, P. (1991). Breast cancer cell kinetics: immunocytochemical determination of growth fractions by monoclonal antibody Ki-67 and correlation with flow cytometric S-phase and with some features of tumor aggressiveness. *Anticancer Res.* 11, 2015-2022.

30. GOLDENBERG, M. M. (1999). Trastuzumab, a recombinant DNA-derived humanized monoclonal antibody, a novel agent for the treatment of metastatic breast cancer. *Clin. $^1$herapeutics* 21, 309-318.

31. GOLDIE, J. H. & COLDMAN, A. J. (1998). *Drug Resistance in Cancer, Mechanisms and Models*. Cambridge: Cambridge University Press.

32. GYLLENBERG, M. & WEBB, G. F. (1989). Quiescence as an explanation of Gompertzian tumor growth. *Growth, Dev. Aging* 53, 25-33.

33. HANDE, K. R. (1996). The importance of drug scheduling in cancer chemotherapy: etoposide as an example. *Stem Cells* 14, 18-24.

34. HARNEVO, L. E. & AGUR, Z. (1991). The dynamics of gene amplification described as a multitype compartmental model and as a branching process. *Math. Biosci.* 103, 115-138.

35. HAUSTERMANS, K., FOWLER, J., GEBOES, K., LERUT, A., VAN CUTSEM, E. & BEGG, A. (1999). Cell kinetic measurements: principles, guidelines for treatment? *Hepato-Gastroenterology* 46, 670-678.

36. HOG CKEL, M., SCHLENGER, K., HOG CKEL, S. & VAUPEL, P. (1999). Hypoxic cervical cancers with low apoptotic index are highly aggressive. *Cancer Res.* 59, 4525-4528.

37. HOFER, E. P., BRUCHER, S., MEWR, K. & TIBKEN, B. (1995). An approach to a biomathematical model of lymphocytopoiesis. *Stem Cells* 13, 290-300.

38. HOKANSON, J. A., BROWN, B. W., THOMPSON, J. R., JANSSON, B. & DREWINKO, B. (1986). Mathematical model for human myeloma relating growth kinetics and drug resistance. *Cell $^1$issue Kinet.* 19, 1-10.

39. HOOGSTRATEN, B., GEORGE, S. L., SAMAL, B., RIVKIN, S. E., CONSTANZI, J. J., BONNET, J. D., THIGPEN, T. & BRAINE, H. (1976). Combination chemotherapy and adriamycin in patients with advanced breast cancer. *Cancer* 38, 13-20.

40. HORTOBAGYI, G. N., BODEY, G. P., BUZDAR, A. U., FRYE, D., LEGHA, S. S., MALIK, R., SMITH, T. L., BLUMENSCHEIN, G. R., YAP, H. & RODRIGUEZ, V. (1987). Evaluation of high-dose versus standard CAF chemotherapy for advanced breast cancer in protected environment units: a prospective randomized study. *J. Clin. Oncol.* 5, 354-364.

41. HRYNIUK, W. M. (1987). Average relative dose intensity and the impact on design of clinical trials. *Semin. Oncol.* 14, 65-74.

42. JOHNSON, P. W. M., THOMPSON, P. I., SEYMOUR, M. T., DEASY, N. P., THURAISINGHAM, R. C., SLEVIN, M. L. & WRIGLEY, P. F. M. (1991). A less toxic regimen of 5-fluorouracil and high-dose folinic acid for advanced gastrointestinal adenocarcinomas. *Br. J. Cancer* 64, 603-605.

43. JORDAN, V. C. & MURPHY, C. S. (1990). Endocrine pharmacology of antiestrogens as antitumor agents. *Endocrine Rev.* 11, 578-597.

44. KILLMANN, S. A. (1968). Acute leukemia: the kinetics of leukemic blast cells in man. Ser. Haematol. *Cell Kinet. Hum. ,eukemia* 1, 38-102.

45. KIM, C. Y., TSAI, M. H., OSMANIAN, C., GRAEBER, T. G., LEE, J. E., GIFFARD, R. G., DIPAOLO, J. A., PEEHL, D. M. & GIACCIA, A. J. (1997). Selection of human cervical epithelial cells that possess reduced apoptotic potential to low-oxygen conditions. *Cancer Res.* 57, 4200-4204.

46. LEE, J. W., GERSUK, G. M., KIENER, P. A., BECKHAM, C., LEDBETTER, J. A. & DEEG, H. J. (1997). HLA-DR-triggered inhibition of hemopoiesis involves Fas/Fas ligand interactions and is prevented by c-kit ligand. *J. Immunol.* 159, 3211-3219.

47. LEITH, J. T. & MICHELSON, S. (1994). Changes in the extents of viable and necrotic tissue, interstitial fluid pressure, and proliferation kinetics in clone. A human colon tumour xenografts as a function of tumour size. *Cell Prolif.* 27, 723-739.

48. LEVASSEUR, L. M., SLOCUM, H. K., RUSTUM, Y. M. & GRECO, W. R. (1998). Modeling of the time-dependency of in vitro drug cytotoxicity and resistance. *Cancer Res.* 58, 5749-5761.

49. LIPPONEN, P. (1999). Apoptosis in breast cancer: relationship with other pathological parameters. *Endocr. Relat. Cancer* 6, 13-16.

50. LONN, U., LONN, S. & STENKVIST, B. (1993). Appearance of amplified thymidylate synthase or dihydrofolate reductase genes in stage-IV breast-cancer patients receiving endocrine treatment. *Int. J. Cancer* 54, 237-242.

51. LORD, B. I. (1997). Biology of haemopoietic stem cell. In: *Stem Cells* (Potten, C. S., ed.), pp. 401-422. San Diego: Academic Press.

52. MACGROGAN, G., MAURIAC, L., DURAND, M., BONICHON, F., TROJANI, M., DE MASCAREL, I. & COINDRE, J. M. (1996). Primary chemotherapy in breast invasive carcinoma: predictive value of the immunohistochemical detection of hormonal receptors p53, c-erB-2, MiB1, pS2 and GST. *Br. J. Cancer* 74, 1458-1465.

53. MARUSIC, M., BAJZER, Z., FREYER, J. P. & VUK-PAVLOVIC, S. (1994). Analysis of growth of muticellular tumour spheroids by mathematical models. *Cell Prolif.* 27, 73-94.

54. MATHE, G. (1998). The kinetics of cancer cells and of HIV1: the problems of cell and virus rebounds and of latency. *Biomed. Pharmacother.* 52, 413-420.

55. MATSUSHIMA, H., GOTO, T., HOSAKA, Y., KITAMURA, T. & KAWABE, K. (1999). Correlation between proliferation, apoptosis, and angiogenesis in prostate carcinoma and their relation to androgen ablation. *Cancer* 85, 1822-1827.

56. MEYER, J. S. (1989). Measurements of cellular proliferation and DNA in breast carcinoma. In: *High-Risk Breast Cancer*. (Ragaz, J. & Ariel, I. M., eds), pp. 141-171. Berlin: Springer-Verlag.

57. MEYN, R. E., STEPHENS, L. C., ANG, K. K., HUNTER, N. R., BROCK, W. A., MILAS, L. & PETERS, L. J. (1993). Heterogeneity in the development of apoptosis in irradiated murine tumours of di!erent histologies. *Int. J. Radiat. Biol.* 64, 583-591.

58. MICHELSON, S. (1993). Mathematical models for multidrug resistance and its reversal. *Cytotechnology* 12, 315-324.

59. MICHELSON, S. & LEITH, J. T. (1993). Tumor heterogeneity: a review of the theory. *Drug News Perspectives* 6, 655-661.

60. MICHELSON, S. & LEITH, J. T. (1996). Host response in tumor growth and progression. *Invasion Metastasis* 16, 235-246.

61. MOLINARI, R., COSTA, A. & VENERONI, S. (1991). Cell kinetics and response to primary intra-arterial chemotherapy in patients with advanced oral cavity tumors. *J. Oral. Pathol. Med.* 20, 32-36.

62. MURRAY, J. M. (1995). An example of the e!ects of drug resistance on the optimal schedule for a single drug in cancer chemotherapy. *IMA J. Math. Appl. Med. Biol.* 12, 55-69.

63. NORTON, L. (1988). A Gompertzian model of human breast cancer growth. *Cancer Res.* 48, 7067-7071.

64. NORTON, L. & SIMON, R. (1977). Tumor size, sensitivity to therapy, and design of treatment schedules. *Cancer ¹reat. Rep.* 61, 1307-1317.

65. NORTON, L. & SIMON, R. (1986). The Norton-Simon hypothesis revisited. *Cancer ¹reat. Rep.* 70, 163-169.

66. O'CONNER, P. M., JACKMAN, J., BAE, I.,MYERS, T. G., FAN, S., MUTOH, M., SCUDIERO, D. A., MONKS, A., SAUSVILLE, E. A., WEINSTEIN, J. N., FRIEND, S., FORNACE, A. J. J. & KOHN, K. W. (1997). Characterization of the p53 tumor supressor pathway in cell lines of the National Cancer Institute anticancer drug screen and correlations with the growth-inhibitory potency of 123 anticancer agents. *Cancer Res.* 57, 4285-4300.

67. PANETTA, J. C. (1997). A mathematical model of drug resistance: heterogeneous tumors. *Math. Biosci.* 147, 41-61.

68. PAPAYANNOPOULOU, T., ABKOWITZ, J. & D'ANDREA, A. (2000). Biology of Erythropoiesis, erythroid di!erentiation, and maturation. In: *Hematology, Basic Principles and Practice*. (Ho!man, R., Benz Jr, E. J., Shattil, S. J., Furie, B., Cohen, H. J., Silberstein, L. E. & McGlave, P., eds), p. 203. New York: Churchill Livingstone.

69. PEGRAM, M. D., LIPTON, A., HAYES, D. F., WEBER, B. L., BASELGA, J. M., TRIPATHY, D., BALY, D., BAUGHMAN, S. A., TWADDELL, T., GLASPY, J. A. & SLAMON, D. J. (1998). Phase II study of receptor-enhanced chemosensitivity using recombinant humanized anti-p185(HER2/neu) monoclonal antibody plus cisplatin in patients with HER2/neu-overexpressing metastatic breast cancer refractory to chemotherapy treatment. *J. Clin. Oncol.* 16, 2659-2671.

70. PRESS, W. H., TEUKOLSKY, S. A., VETTERLING, W. T. & FLANNERY, B. P. (1992). *Numerical Recipies in C*, $2^{nd}$ Edn. Cambridge: Cambridge University Press. PRICE, L. A. (1987). Safer cancer chemotherapy using a kinetically-based experimental approach: higher dose intensity with reduced toxicity. *Cancer ¹reat. Rev.* 14, 215-223.

71. SCHIMKE, R. T. (1984). Gene amplification, drug resistance, and cancer. *Cancer Res.* 44, 1735-1742. SHAH, A., MACDONALD, W., GOLDIE, J., GUDAUSKAS, G. & BRISEBOIS, B. (1985). 5 FUinfusion in advanced colorectal cancer: a comparison of three dose schedules. *Cancer* $^1$*reat. Rep.* 69, 739-742.

72. SILVESTRINI, R., DAIDONE, M. G., VALENTINIS, B., FERRARIS, C., DI RE, E. & RASPAGLIESI, F. (1992). Potentials of cell kinetics in the management of patients with ovarian cancers. *Eur. J. Cancer* 28, 386-390.

73. SILVESTRINI, R., DAIDONE, M. G., LUISI, A., MASTORE, M., LEUTNER, M. & SALVADORI, B. (1997). Cell proliferation in 3800 node-negative breast cancers: consistency over time of biological and clinical information provided by 3Hthymidine labelling index. *Int. J. Cancer (Pred. Oncol.)* 74, 122-127.

74. SILVESTRINI, R., LUISI, A., ZAMBETTI, M., CIPRIANI, S., VALAGUSSA, P., BONADONNA, G. & DAIDONE, M. G. (2000). Cell proliferation and outcome following doxorubicin plus CMF regimens in node-positive breast cancer. *Int. J. Cancer* 87, 405-411.

75. SINICROPE, F. A., HART, J., HSU, H., LEMOINE, M., MICHELASSI, F. & STEPHENS, L. C. (1999). Apoptotic and mitotic indices predict survival rates in lymph nodenegative colon carcinomas. *Clin. Cancer Res.* 5, 1793-1804.

76. SKIPPER, H. E., SCHABEL JR., F. M. & WILCOX, W. S. (1967). Experimental evaluation of potential anticancer agents. XXI, Scheduling or arabinosyl cytosine to take advantage of its S-phase specificity against leukemia cells. *Cancer Chemother. Rep.* 51, 125-141.

77. SOBRERO, A. F., ASCHELE, C. & BERTINO, J. R. (1997). Fluorouracil in colorectal cancer*a tale of two drugs: implications for biochemical modulation. *J. Clin. Oncol.* 15, 368-381.

78. SOUHAMI, R. L. (1995). Will increases in dose intensity improve outcome: con. *Am. J. Med.* 99, 71S-76S.

79. SPEER, J. F., PETROSKY, V. E., RETSKY, M. W. & WARDWELL, R. H. (1984). A stochastic numerical model of breast cancer growth that simulates clinical data. *Cancer Res.* 44, 4124-4130.

80. SPRATT, J. A., VON FOURNIER, D., SPRATT, J. S. & WEBER, E. E. (1993). Decelerating growth and human breast cancer. *Cancer* 71, 2013-2019.

81. SPRATT, J. S., GREENBERG, R. A. & HEUSER, L. S. (1986). Geometry, growth rates and duration of cancer and carcinoma in situ of the breast before detection by screening. *Cancer Res.* 46, 970-974.

82. STAPLETON, A. M., ZBELL, P., KATTAN, M. W. G. Y., WHEELER, T. M., SCARDINO, P. T. & THOMPSON, T. C. (1998). Assessment of the biologic markers p53, Ki-67, and apoptotic index as predictive indicators of prostate carcinoma recurrence after surgery. *Cancer* 82, 168-175.

83. STEEL, G. G. (1977). $^1$*he Growth Kinetics of* $^1$*umors*. Oxford: Oxford University Press.

84. TANNOCK, I. (1978). Cell kinetics and chemotherapy: a critical review. *Cancer* $^1$*reat. Rep.* 62, 1117-1133.

85. TOUSSAINT, C., IZZO, J., SPIELMANN, M., MERLE, S., MAYLEVIN, F., ARMAND, J. P., LACOMBE, D., TURSZ, T., SUNDERLAND, M., CHABOT, G. G. & CVITKOVIC, E. (1994). Phase I/II trial of continuous infusion vinorelbine for advanced breast cancer. *J. Clin. Oncol.* 12, 2102-2112.

86. VAN PUTTEN, L. M. (1974). Are cell kinetic data relevant for the design of tumour chemotherapy schedules? *Cell* $^1$*issue Kinet.* 7, 493-504.

87. WOOD, W. C., BUDMAN, D. R., KORZON, A. H., COOPER, M. R., YOUNGER, J., HART, R. D., MOORE, A., ELLERTON, J. A., NORTON, L., FERREE, C. R., BALLOW, A. C., FREI III, E., & HENDERSON, I. C. (1994). Dose and dose intensity of adjuvant chemotherapy for stage II, nodepositive breast carcinoma. *N. Engl. J. Med.* 330, 1253-1259.

88. XIE, X., CLAUSEN, O. P. F., ANGELIS, P. D. & BOYSEN, M. (1999). The prognostic value of spontaneous apoptosis, Bax, Bcl-2, and p53 in oral squamous cell carcinoma of the tongue. *Cancer* 86, 913-920.

89. YIP, D., AHMAD, A., KARAPETIS, C. S., HAWKINS, C. A. & HARPER, P. G. (1999). Matrix metalloproteinase inhibitors: applications in oncology. *Investigational New Drugs* 17, 387-399.

All publications mentioned hereinabove are hereby incorporated in their entireties. While the foregoing invention has been described in some detail for purposes of clarity and understanding, such description is not intended to be limiting. Modifications and changes may become apparent to those skilled in the art without departing from the true scope of the invention in the appended claims.

I claim:

1. A method for tailoring multidrug chemotherapy treatment regimens to individual patients with diseased cells exhibiting evolution of resistance to drugs used in such treatments, said method comprising the steps of:

providing a set of differential equations representing a mathematical model of rates of population change of proliferating and quiescent diseased cells, said mathematical model including parameters corresponding to cell kinetics and evolution of drug resistance of the diseased cells to cell-cycle phase-specific cytotoxic drugs, cell-cycle phase non-specific cytotoxic drugs, and cytostatic drugs;

obtaining cell kinetic parameter values from an individual patient including proliferative index, apoptotic index, S-phase fraction, cell cycle time, and level of drug resistance;

using the cell kinetic parameter values obtained from the patient to solve the set of differential equations of the mathematical model to determine a plurality of treatment regimens for the patient, each of said treatment regimens having a quantitative efficacy value associated therewith representing the efficacy thereof in reducing the diseased cell population of the patient; and selecting one of the treatment regimens having an efficacy value that is desirable for treating the patient, said selected treatment regimen thereby being tailored to the patient.

2. The method of claim 1, wherein the set of differential equations representing the mathematical model further incorporates a Gompertzian curve for modeling tumor growth.

3. The method of claim 1, wherein the set of differential equations representing the mathematical model additionally includes parameters corresponding to evolution of cell kinetics.

4. The method of claim 1, wherein the set of differential equations representing the mathematical model additionally includes parameters corresponding to a transition rate from proliferating to quiescent compartments, and a transition rate from quiescent to proliferating compartments, with the proliferative and apoptotic indices obtained from the patient used to determine transition rate from proliferating to quiescent compartments.

5. The method of claim 1,
wherein the set of differential equations representing the mathematical model additionally includes a parameter corresponding to a time-dependent drug concentration.

6. The method of claim 1,
wherein the set of differential equations representing the mathematical model additionally includes a parameter corresponding to relative average dose intensity, for modeling toxicity.

7. The method of claim 1,
wherein the efficacy value is the probability of survival.

8. A computer program product comprising:
a computer-readable medium having a computer-readable set of instructions embodied in said medium for enabling a computer system to provide multi-drug chemotherapy cancer treatment alternatives to individual patients based on tumor cell kinetics of the patient, the set of instructions comprising:
a system model code for causing the computer system to provide a set of differential equations representing a mathematical model of rates of population change of proliferating and quiescent diseased cells, said mathematical model including parameters corresponding to cell kinetics and evolution of drug resistance of the diseased cells to cell-cycle phase-specific cytotoxic drugs, cell-cycle phase non-specific cytotoxic drugs, and cytostatic drugs;
an input code for causing the computer system to receive tumor cell kinetic parameters obtained from the individual patient, the cell kinetic data including proliferative index, apoptotic index, S-phase fraction, cell cycle time, and level of drug resistance;
a processing code for causing the computer system to solve the set of differential equations of the mathematical model using the tumor cell kinetic parameters obtained from the patient to produce a plurality of alternative treatment regimens for the patient, each of said treatment regimens having a quantitative efficacy value associated therewith representing the efficacy thereof in reducing the tumor cell population of the patient; and
an output code for causing the computer system to present the plurality of treatment regimens so that one of the treatment regimens may be selected based on an efficacy value that is desirable for the patient.

9. A system for providing multi-drug chemotherapy cancer treatment alternatives to individual patients based on tumor cell kinetics of the patient, said system comprising:
an input module for receiving cell kinetic data obtained from an individual patient, the cell kinetic data including proliferative index, apoptotic index, S-phase fraction, cell cycle time, and level of drug resistance;
a system processor for using the cell kinetic data obtained from the patient in the mathematical model to solve a set of differential equations representing a mathematical model of rates of population change of proliferating and quiescent tumor cells, said mathematical model including parameters corresponding to cell kinetics and evolution of drug resistance of the tumor cells to cell-cycle phase-specific cytotoxic drugs, cell-cycle phase non-specific cytotoxic drugs, and cytostatic drugs, and to determine for a plurality of treatment regimens for the patient, each of said treatment regimens having a quantitative efficacy value associated therewith representing the efficacy thereof in reducing the tumor cell population of the patient; and
an output module for presenting the plurality of treatment regimens, so that one of the treatment regimens may be selected based on an efficacy value that is desirable for the patient.

10. The system of claim 9,
wherein the set of differential equations representing the mathematical model additionally includes parameters corresponding to evolution of cell kinetics.

11. The system of claim 9,
wherein the set of differential equations representing the mathematical model additionally includes parameters corresponding to a transition rate from proliferating to quiescent compartments, and a transition rate from quiescent to proliferating compartments, with the proliferative and apoptotic indices obtained from the patient used to determine transition rate from proliferating to quiescent compartments.

12. The system of claim 9,
wherein the set of differential equations representing the mathematical model additionally includes a parameter corresponding to a time-dependent drug concentration.

13. The system of claim 9,
wherein the set of differential equations representing the mathematical model additionally includes a parameter corresponding to relative average dose intensity, for modeling toxicity.

14. The system of claim 9,
wherein the efficacy value is the probability of survival.

* * * * *